(12) United States Patent
Kriesel et al.

(10) Patent No.: US 7,833,195 B2
(45) Date of Patent: *Nov. 16, 2010

(54) FLUID DISPENSING APPARATUS

(75) Inventors: Marshall S. Kriesel, St. Paul, MN (US); Joshua W. Kriesel, San Francisco, CA (US); Thomas N. Thompson, Richfield, MN (US)

(73) Assignee: BioQuiddity, Inc., San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/980,963

(22) Filed: Oct. 30, 2007

(65) Prior Publication Data

US 2008/0228129 A1 Sep. 18, 2008

Related U.S. Application Data

(63) Continuation-in-part of application No. 11/725,220, filed on Mar. 14, 2007.

(51) Int. Cl.
*A61M 37/00* (2006.01)
*B67D 7/06* (2010.01)
*A61N 1/30* (2006.01)

(52) U.S. Cl. .................... 604/133; 222/183; 604/19

(58) Field of Classification Search .................. 604/132; 222/153.06, 541.6, 541.7, 386.5
See application file for complete search history.

(56) References Cited

U.S. PATENT DOCUMENTS

| | | | |
|---|---|---|---|
| 2,236,084 A | | 3/1941 | Brown |
| 5,632,315 A | * | 5/1997 | Rose .......................... 141/329 |
| 6,050,400 A | * | 4/2000 | Taskis et al. ................. 206/204 |
| 6,236,634 B1 | | 5/2001 | Kriesel et al. |
| 6,679,304 B1 | * | 1/2004 | Vacca .......................... 141/313 |
| 2001/0054627 A1 | * | 12/2001 | Lin et al. .................. 222/386.5 |
| 2005/0038387 A1 | * | 2/2005 | Kriesel et al. ................ 604/133 |
| 2006/0030819 A1 | * | 2/2006 | Young et al. .................. 604/187 |

* cited by examiner

*Primary Examiner*—Kevin C Sirmons
*Assistant Examiner*—Brandy C Scott

(57) ABSTRACT

A compact fluid dispenser for use in controllably dispensing fluid medicaments, such as antibiotics, blood clotting agents, analgesics, and like medicinal agents from collapsible containers at a uniform rate. The dispenser includes a novel stored energy source that is provided in the form of a compressible-expandable member that functions to continuously and uniformly expel fluid from the apparatus reservoir. The apparatus further includes a novel fluid flow control assembly that precisely controls the flow of the medicament solutions from the apparatus reservoir to the patient.

28 Claims, 38 Drawing Sheets

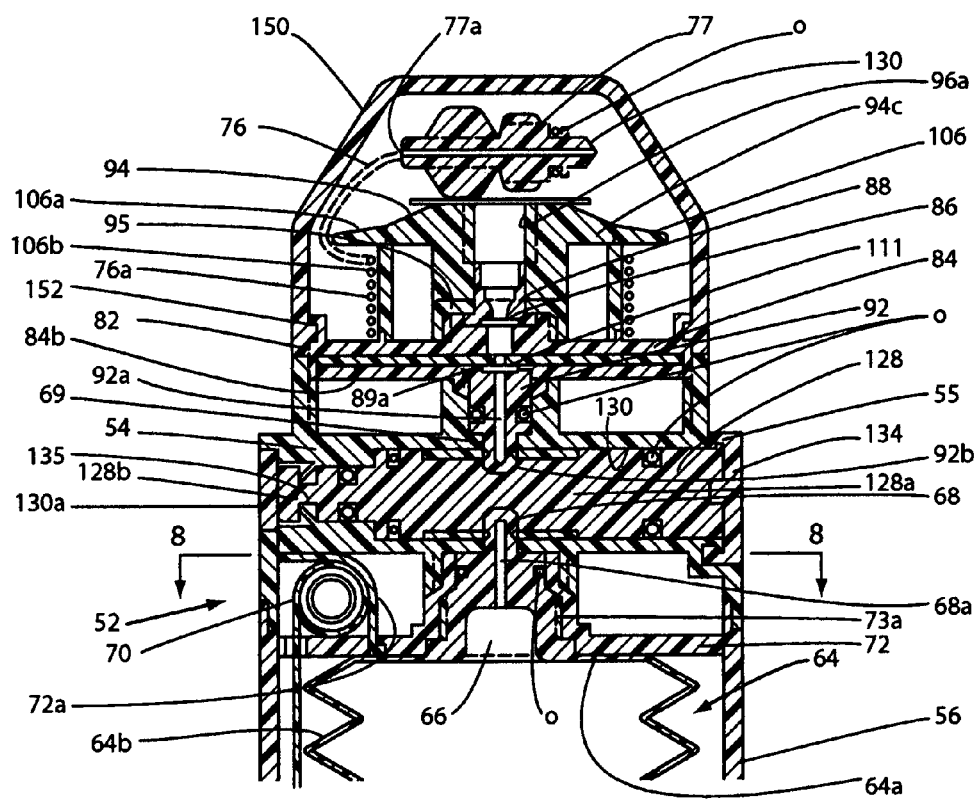
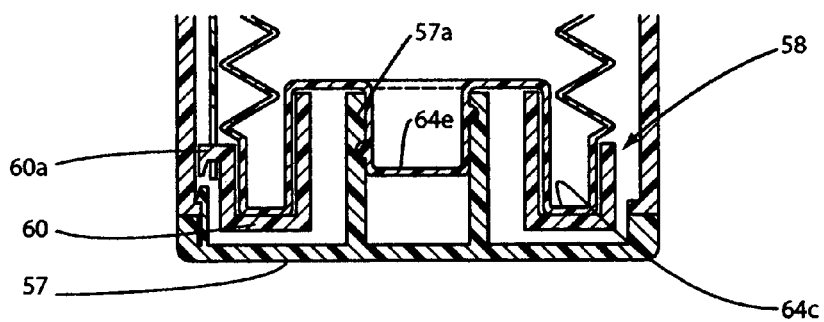
FIG. 3

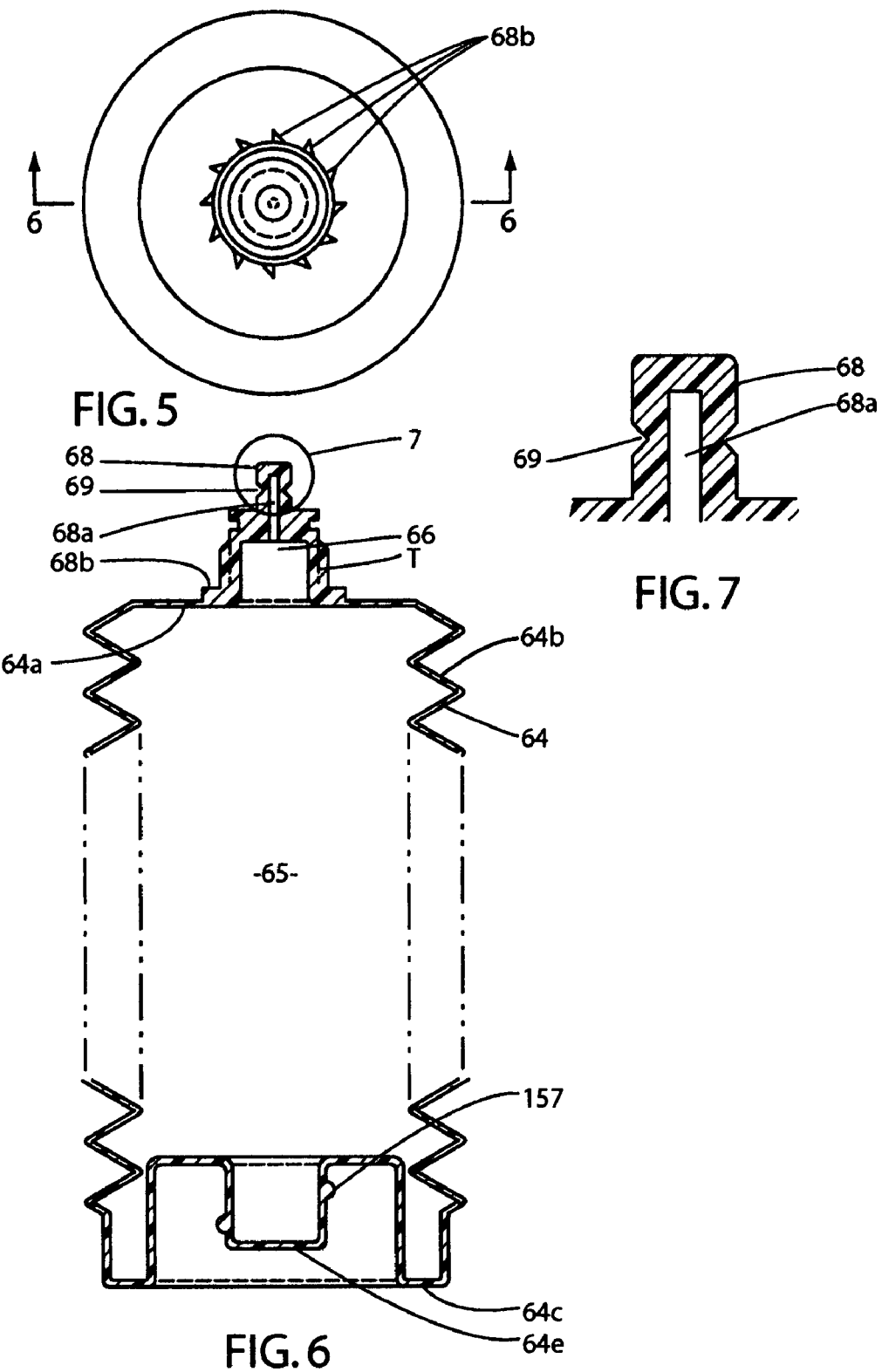

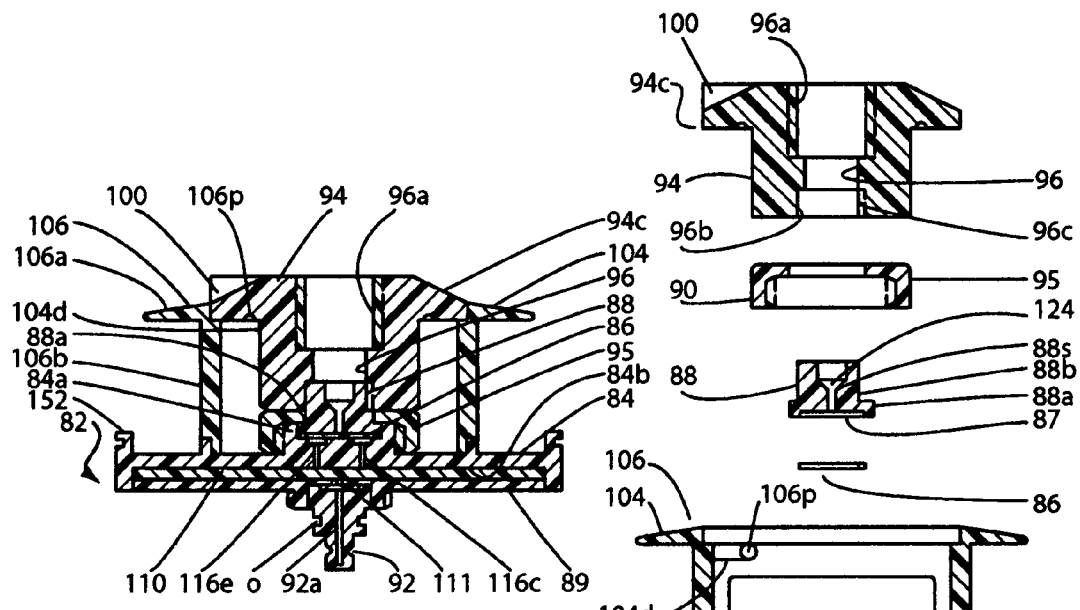
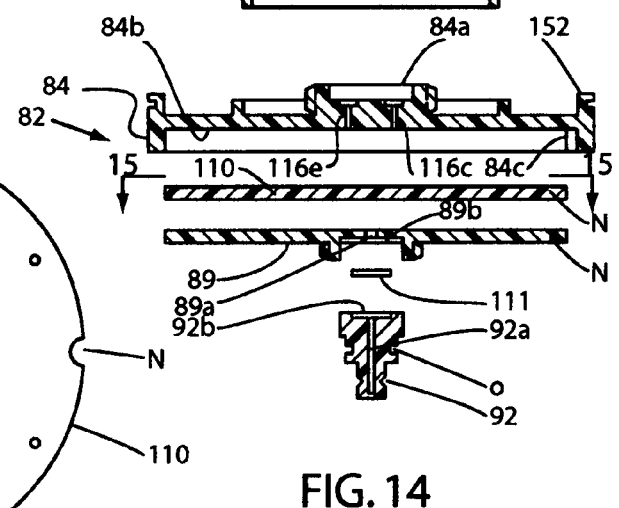
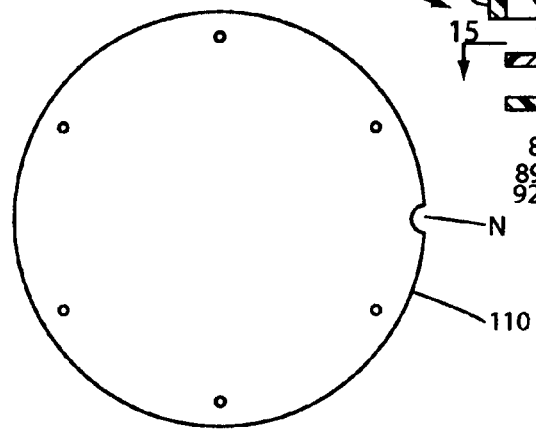
FIG. 13
FIG. 14
FIG. 15

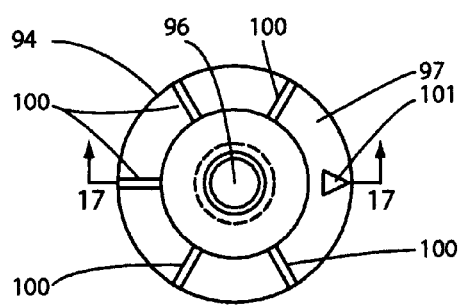
FIG. 16
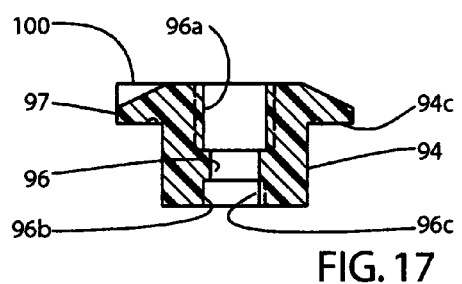
FIG. 17
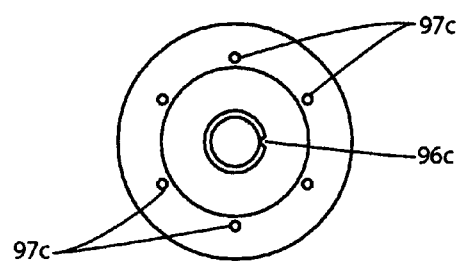
FIG. 18
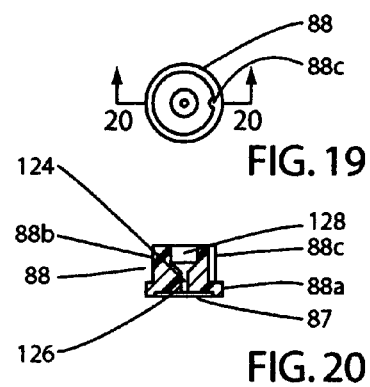
FIG. 19
FIG. 20
FIG. 21
FIG. 22
FIG. 23
FIG. 24
FIG. 25

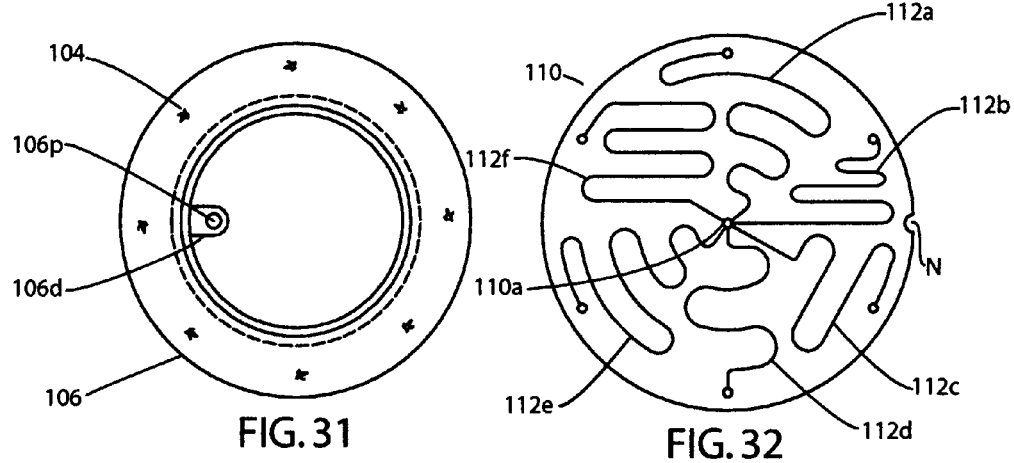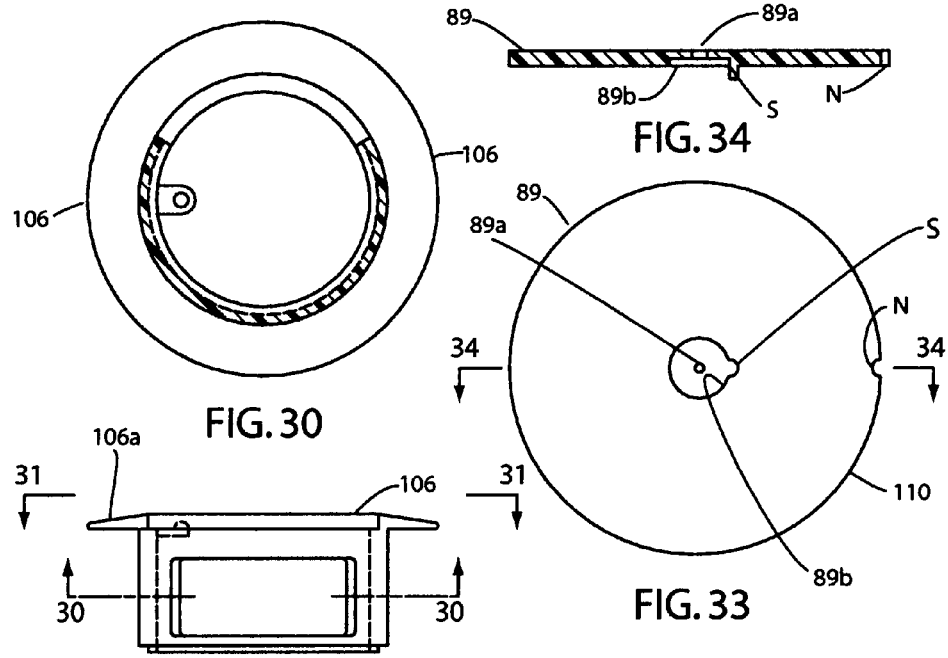

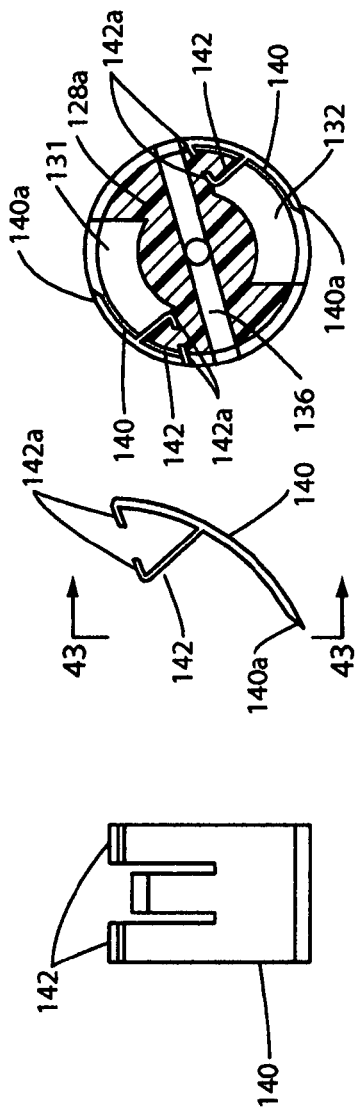
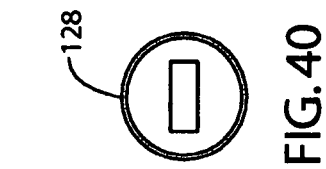
FIG. 40
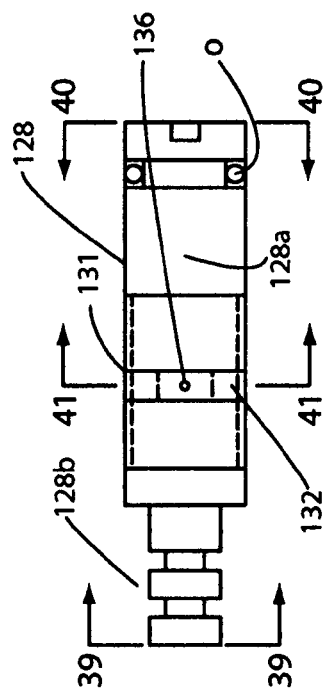
FIG. 41
FIG. 42
FIG. 38
FIG. 43
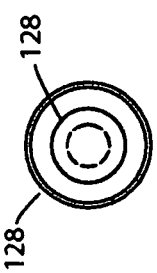
FIG. 39

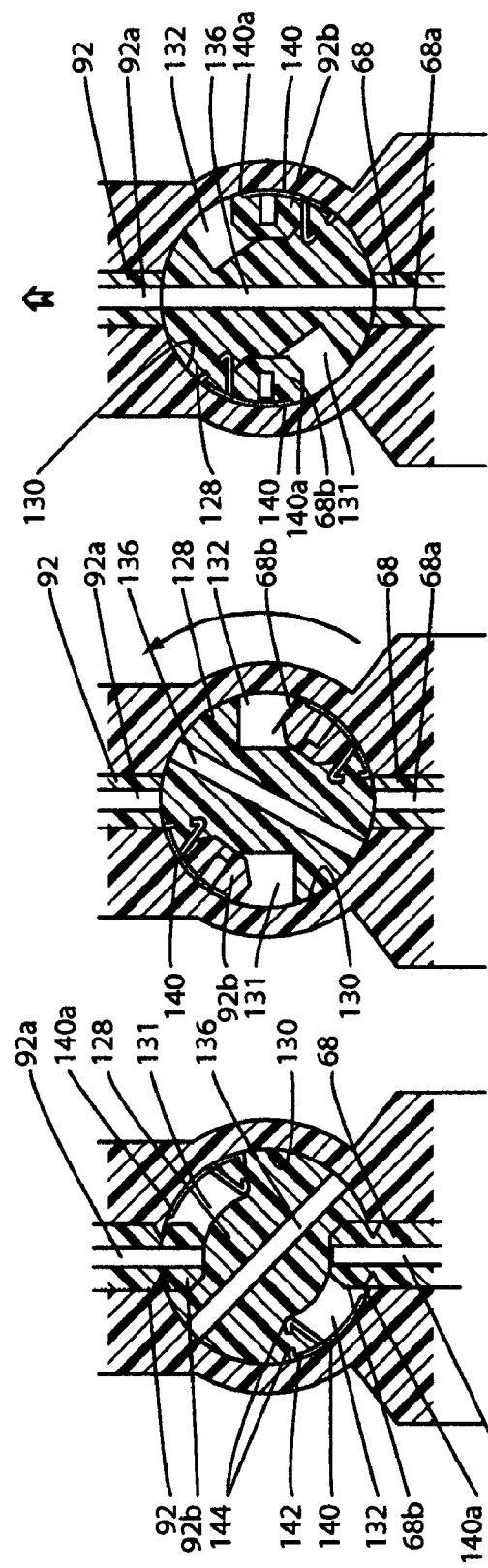

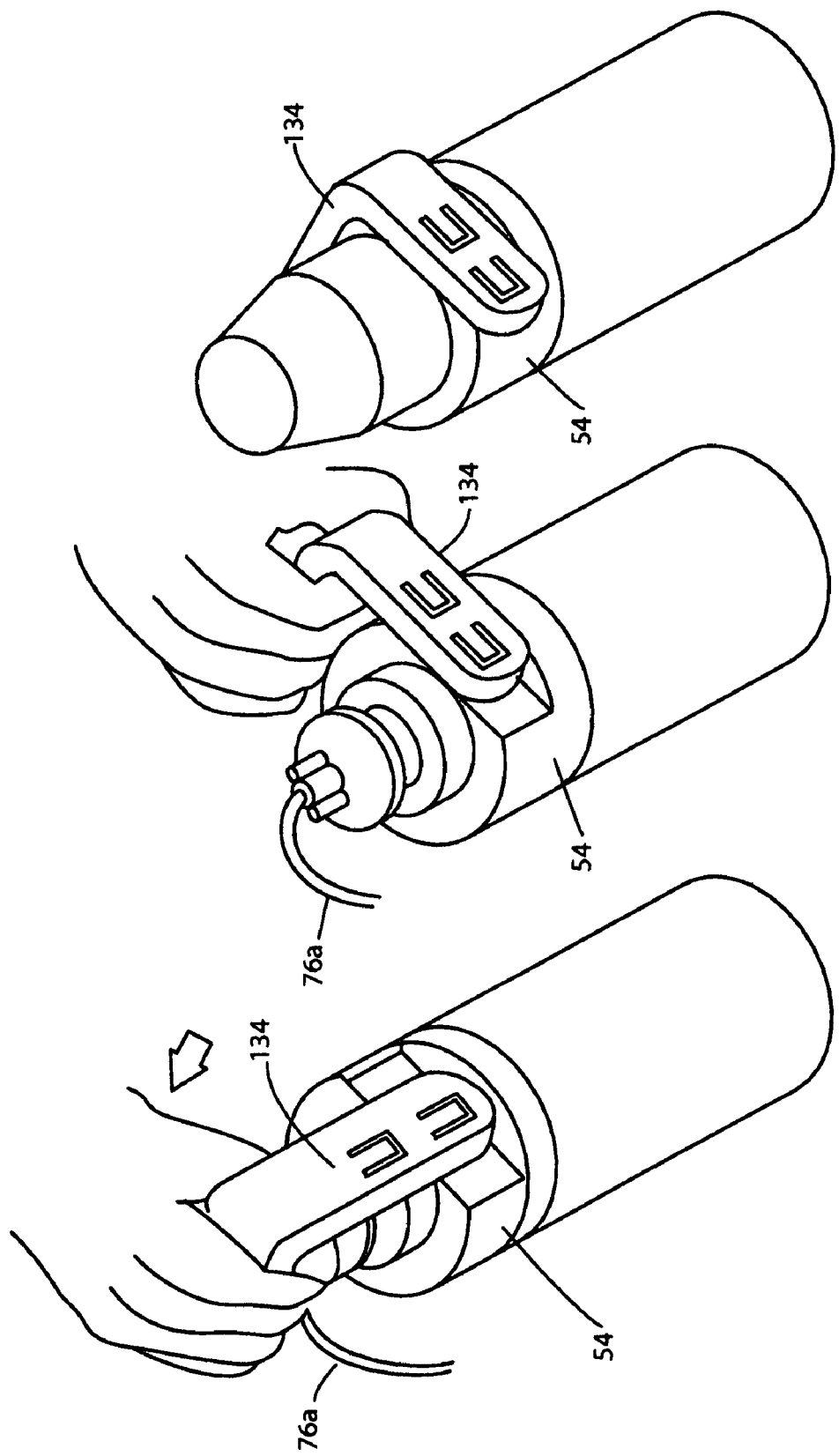

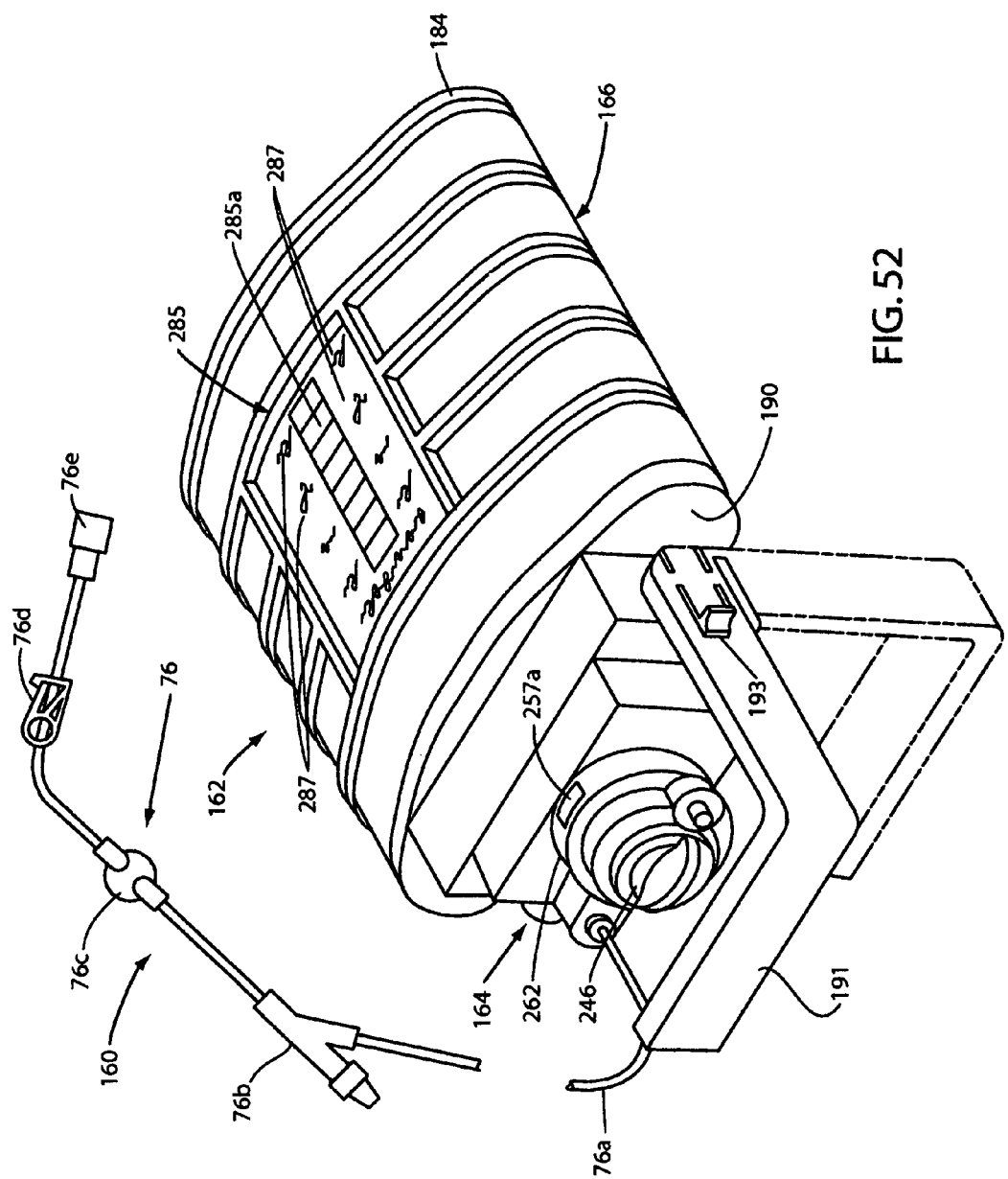

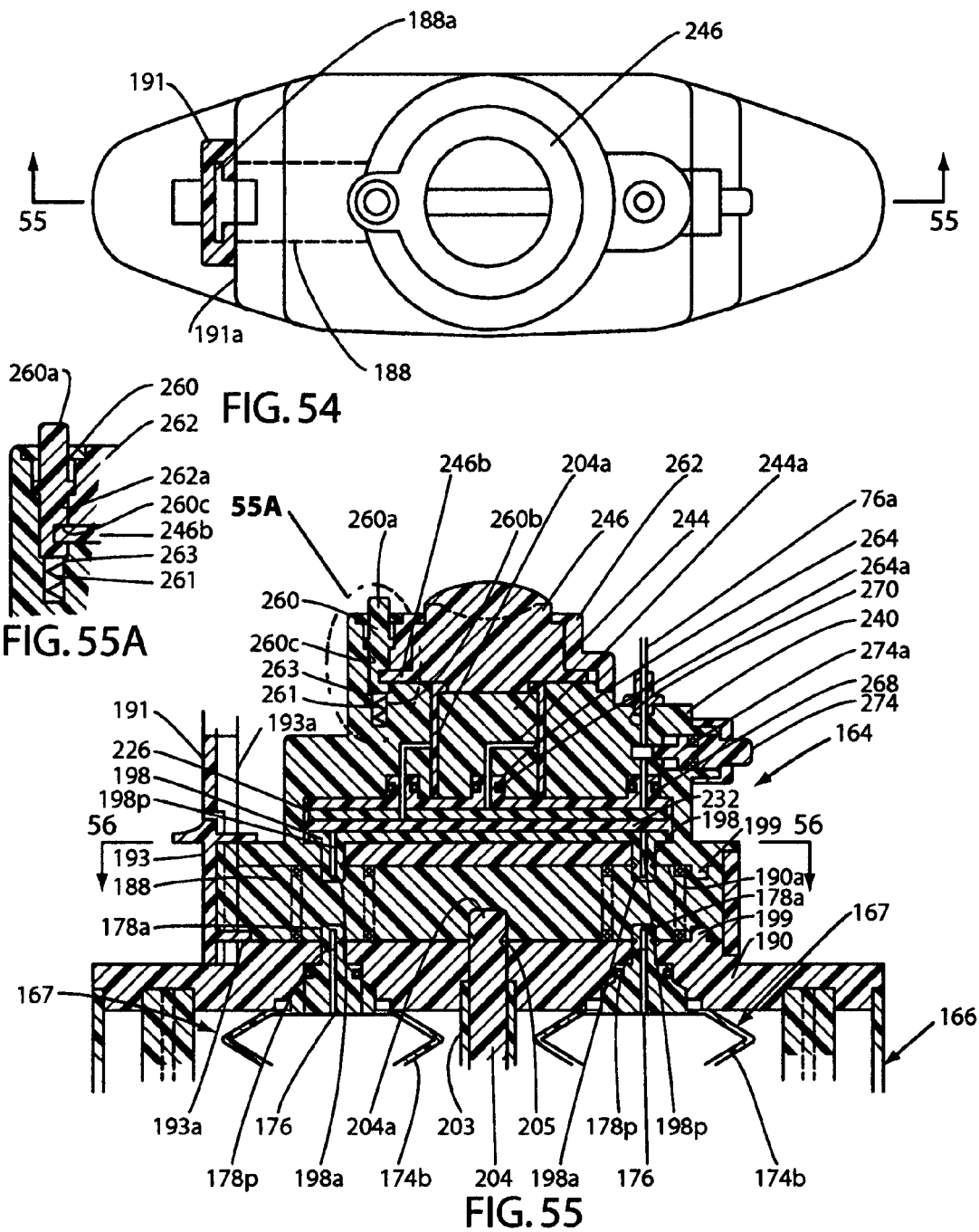

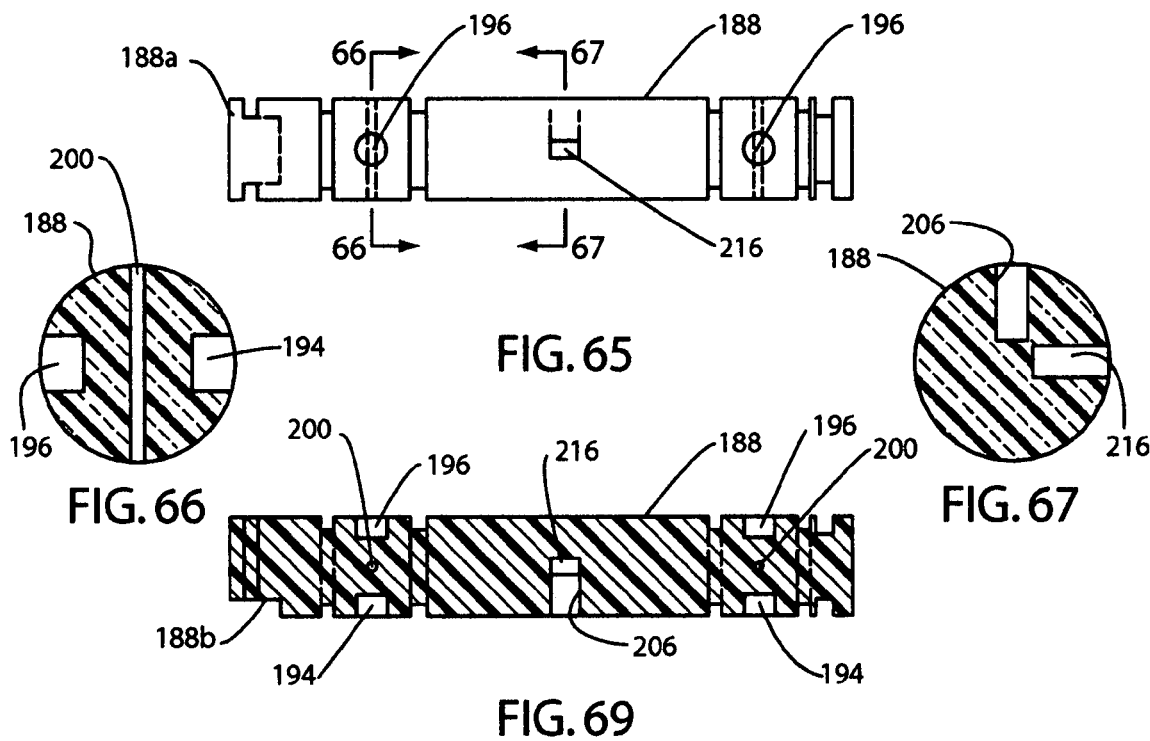
FIG. 65
FIG. 66
FIG. 67
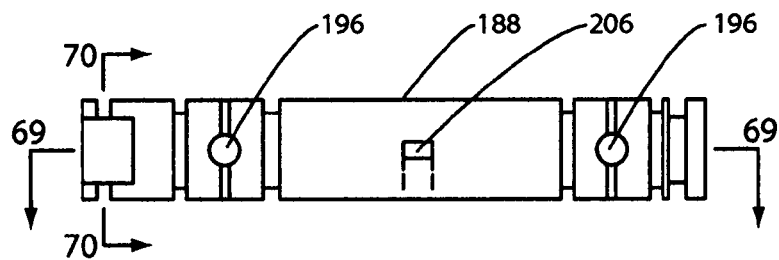
FIG. 69
FIG. 68
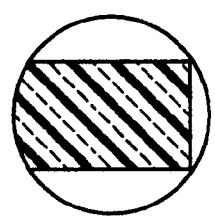
FIG. 70

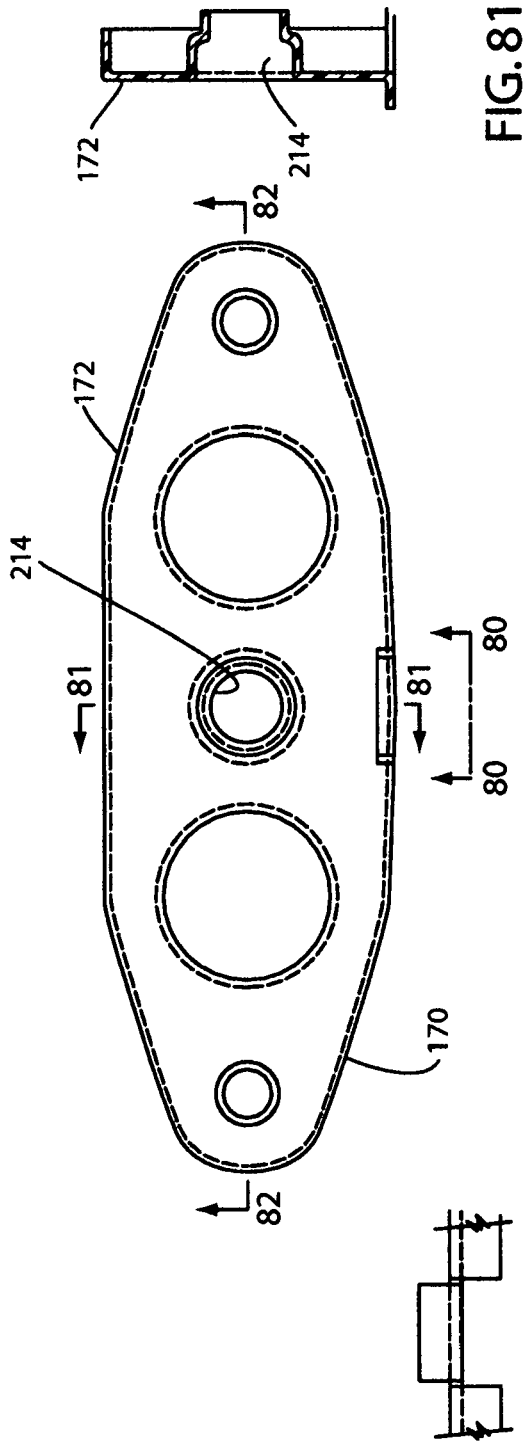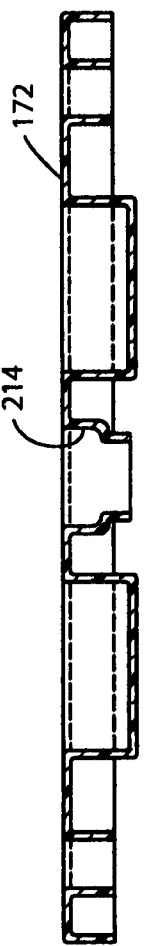

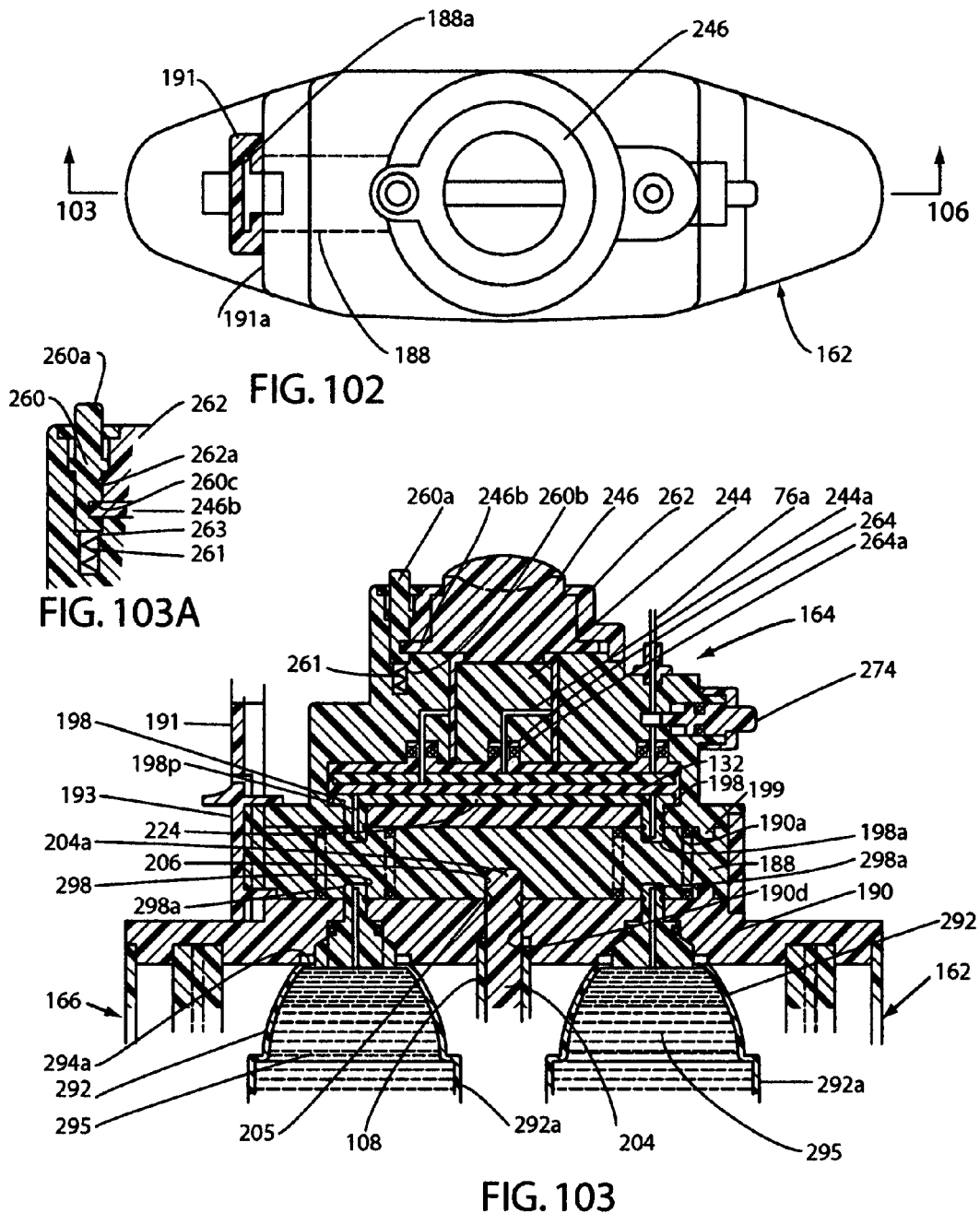

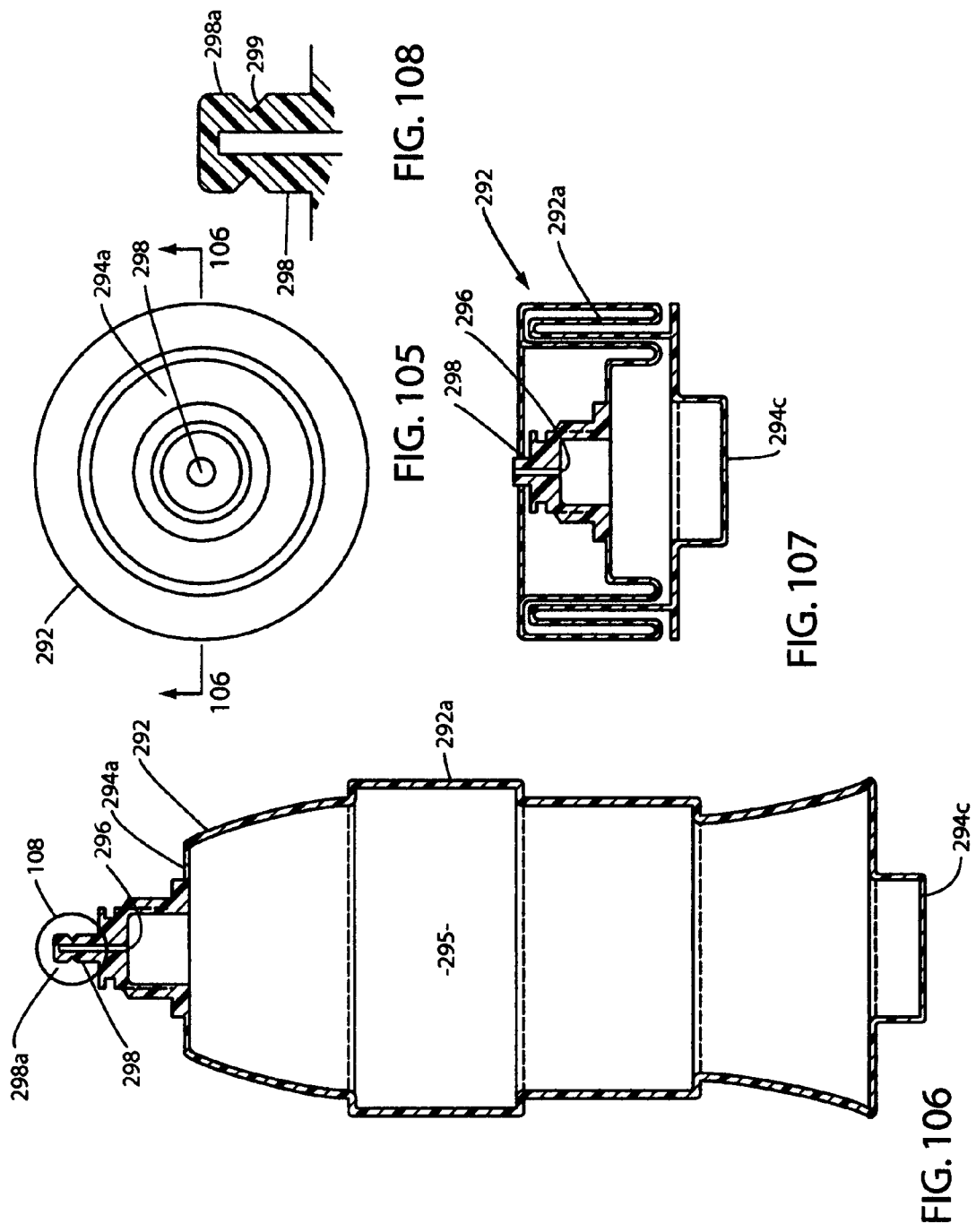

FLUID DISPENSING APPARATUS

This is a Continuation-In-Part of co-pending Application U.S. Ser. No. 11/725,220 filed Mar. 14, 2007.

FIELD OF THE INVENTION

The present invention relates generally to fluid dispensing apparatus. More particularly, the invention concerns medicament dispensers for dispensing medicinal fluids to ambulatory patients.

DISCUSSION OF THE PRIOR ART

A number of different types of medicament dispensers for dispensing medicaments to ambulatory patients have been suggested in the past. Many of the devices seek either to improve or to replace the traditional gravity flow and hypodermic syringe methods which have been the standard for delivery of liquid medicaments for many years.

The prior art gravity flow methods typically involve the use of intravenous administration sets and the familiar flexible solution bag suspended above the patient. Such gravametric methods are cumbersome, imprecise and require bed confinement of the patient. Periodic monitoring of the apparatus by the nurse or doctor is required to detect malfunctions of the infusion apparatus. Accordingly, the prior art devices are not well suited for use in those instances where the patient must be transported to a remote facility for treatment.

With regard to the prior art, one of the most versatile and unique fluid delivery apparatus developed in recent years is that developed by one of the present inventors and described in U.S. Pat. No. 5,205,820. The components of this novel fluid delivery apparatus generally include: a base assembly, an elastomeric membrane serving as a stored energy means, fluid flow channels for filling and delivery, flow control means, a cover, and an ullage which comprises a part of the base assembly.

Another prior art patent issued to one of the present applicants, namely U.S. Pat. No. 5,743,879, discloses an injectable medicament dispenser for use in controllably dispensing fluid medicaments such as insulin, anti-infectives, analgesics, oncolylotics, cardiac drugs, biopharmaceuticals, and the like from a pre-filled container at a uniform rate. The dispenser, which is quite dissimilar in construction and operation from that of the present invention, includes a stored energy source in the form of a compressively deformable, polymeric elastomeric member that provides the force necessary to controllably discharge the medicament from a pre-filled container, which is housed within the body of the device. After having been deformed, the polymeric, elastomeric member will return to its starting configuration in a highly predictable manner.

SUMMARY OF THE INVENTION

By way of brief summary, one form of the dispensing device of the present invention for dispensing medicaments to a patient comprises a supporting structure; a carriage assembly interconnected with the supporting structure for movement between a first position and a second position; a collapsible reservoir carried by the carriage assembly, the collapsible reservoir having an outlet port; guide means connected to the supporting structure for guiding travel of the carriage assembly between the first position and said second positions; a stored energy source operably associated with the carriage assembly for moving the carriage assembly between the first and second positions; and an administration set, including an administration line, interconnected with the outlet port of the collapsible reservoir.

With the forgoing in mind, it is an object of the present invention to provide a compact fluid dispenser for use in controllably dispensing fluid medicaments, such as, antibiotics, blood clotting agents, analgesics, and like medicinal agents from pre-filled or field-filled containers at a uniform rate.

Another object of the invention is to provide a small, compact fluid dispenser of simple construction that can be used in the field with a minimum amount of training.

Another object of the invention is to provide a dispenser in which a stored energy source is provided in the form of a compressible, expandable or retractable member of novel construction that provides the force necessary to continuously and uniformly expel fluid from the device reservoir.

Another object of the invention is to provide a dispenser of the class described which includes a fluid flow control assembly that precisely controls the flow of the medicament solution to the patient.

Another object of the invention is to provide a dispenser that includes precise variable flow rate selection.

Another object of the invention is to provide a fluid dispenser of simple construction, which embodies a pair of spaced-apart, collapsible, pre-filled drug containers that contain the beneficial agents to be delivered to the patient.

Another object of the invention is to provide a fluid dispenser as described in the preceding paragraph in which the stored energy means comprises a plurality of spaced-apart coil springs.

Another object of the invention is to provide a dispenser of the class described which includes a novel carriage locking mechanism for releasably locking the carriage in a first position.

Another object of the invention is to provide a fluid dispenser of the class described which is compact, lightweight, is easy for ambulatory patients to use, is fully disposable, and is extremely reliable in operation.

Another object of the invention is to provide a fluid dispenser as described in the preceding paragraphs that is easy and inexpensive to manufacture in large quantities.

BRIEF DESCRIPTION OF THE DRAWINGS

FIG. 3 is an enlarged, longitudinal, cross-sectional view of the fluid dispensing apparatus illustrated in FIG. 1.

FIG. 5 is a top plan view of the fluid reservoir assembly of the invention.

FIG. 6 is a cross-sectional view taken along lines 6-6 of FIG. 5.

FIG. 7 is an enlarged cross-sectional view of the area designated in FIG. 6 by the numeral "7".

FIG. 13 is a cross-sectional view of the rate control assembly depicted in FIG. 12 as it appears in an assembled configuration.

FIG. 14 is an exploded, cross-sectional view of the rate control assembly illustrated in FIG. 13.

FIG. 15 is a view taken along lines 15-15 of FIG. 14.

FIG. 16 is a top plan view of the selector knob of the present invention for rotating the selector member in a manner to select the rate of fluid flow to the patient.

FIG. 17 is a cross-sectional view taken along lines 17-17 of FIG. 16.

FIG. 18 is a bottom plan view of the selector knob shown in FIG. 17.

FIG. 19 is a top plan view of the selector member of the apparatus which is rotated by the selector knob.

FIG. 20 is a cross-sectional view taken along lines 20-20 of FIG. 19.

FIG. 21 is a bottom plan view of the selector member shown in FIG. 20.

FIG. 22 is front view of the selector element of the rate control means of the invention.

FIG. 23 is a bottom plan view of the selector element.

FIG. 24 is a top plan view of the nipple portion of one of the rate control covers of the rate control assembly.

FIG. 25 is a cross-sectional view taken along lines 25-25 of FIG. 24.

FIG. 29 is a side-elevational view of the selector member housing of the apparatus.

FIG. 30 is a cross-sectional view taken along lines 30-30 of FIG. 29.

FIG. 31 is a view taken along lines 31-31 of FIG. 29.

FIG. 32 is a bottom plan view of the rate control plate of the rate control assembly.

FIG. 33 is a top plan view of the cover member 89 of the rate control assembly.

FIG. 34 is a cross-sectional view taken along lines 34-34 of FIG. 33.

FIG. 38 is a side-elevational view of one form of the control shaft of the flow control means of the invention.

FIG. 39 is a view taken along lines 39-39 of FIG. 38.

FIG. 40 is a view taken along lines 40-40 of FIG. 38.

FIG. 41 is an enlarged cross-sectional view taken along lines 41-41 of FIG. 38.

FIG. 42 is an enlarged, side-elevational view of one form of the spring knife of the invention that is carried within cavities formed in the control shaft as shown in FIG. 41.

FIG. 43 is a view taken along lines 43-43 of FIG. 42.

FIG. 44 is an enlarged, cross-sectional view of a portion of the support structure and of the control shaft of the apparatus illustrating the appearance of the components in their starting position.

FIG. 45 is a cross-sectional view, similar to FIG. 44, but showing the appearance of the components after the initial rotation of the control shaft from a first position to a second position.

FIG. 46 is a cross-sectional view, similar to FIG. 45, but showing the appearance of the components after further rotation of the control shaft from the second position to a third, final position.

FIG. 47 is a generally perspective, diagrammatic view showing the operating handle of the apparatus in its starting position.

FIG. 48 is a generally perspective, diagrammatic view illustrating the gripping of the apparatus handle by the operator.

FIG. 49 is a generally perspective, diagrammatic view illustrating the movement of the operating handle by the operator to open the fluid flow path between the reservoir and the rate control means of the invention.

FIG. 52 is a generally perspective, top view of one form of the fluid dispensing apparatus of the present invention for dispensing medicaments to a patient.

FIG. 54 is an enlarged, top plan view of the dispensing apparatus illustrated in FIG. 52.

FIG. 55 is a fragmentary, cross-sectional view taken along lines 55-55 of FIG. 54 showing only the upper portion of the apparatus shown in FIG. 54.

FIG. 55A is a cross-sectional view of the area designated in FIG. 55 as "55A".

FIG. 65 is a top plan view of the operating shaft of the apparatus of the invention shown in FIG. 52.

FIG. 66 is a greatly enlarged, cross-sectional view taken along lines 66-66 of FIG. 65.

FIG. 67 is a greatly enlarged, cross-sectional view taken along lines 67-67 of FIG. 65.

FIG. 68 is a bottom plan view of the operating shaft of the apparatus of the invention shown in FIG. 52.

FIG. 69 is a cross-sectional view taken along lines 69-69 of FIG. 68.

FIG. 70 is a greatly enlarged, cross-sectional view taken along lines 70-70 of FIG. 68.

FIG. 79 is a top plan view of the reservoir carriage of the apparatus of the invention shown in FIG. 52.

FIG. 80 is a view taken along lines 80-80 of FIG. 79.

FIG. 81 is a cross-sectional view taken along lines 81-81 of FIG. 79.

FIG. 82 is a cross-sectional view taken along lines 82-82 of FIG. 70.

FIG. 102 is an enlarged, top plan view of the dispensing apparatus illustrated in FIG. 101.

FIG. 103 is a fragmentary, cross-sectional view taken along lines 103-103 of FIG. 102 showing the upper portion of the apparatus.

FIG. 103A is a fragmentary, cross-sectional view of the area designated in FIG. 103 as "103A".

FIG. 105 is a top plan view of one of the fluid containers of this latest form of the apparatus of the invention shown in FIG. 101.

FIG. 106 is a cross-sectional view taken along lines 106-106 of FIG. 105.

FIG. 107 is a cross-sectional view, similar to FIG. 106, but showing the container in a collapsed configuration as it appears after the fluid in the fluid reservoir of the container has been dispensed to the patient.

FIG. 108 is a greatly enlarged, cross-sectional view of the area designated in FIG. 106 as "108".

DESCRIPTION OF THE INVENTION

Definitions

Figure 1:
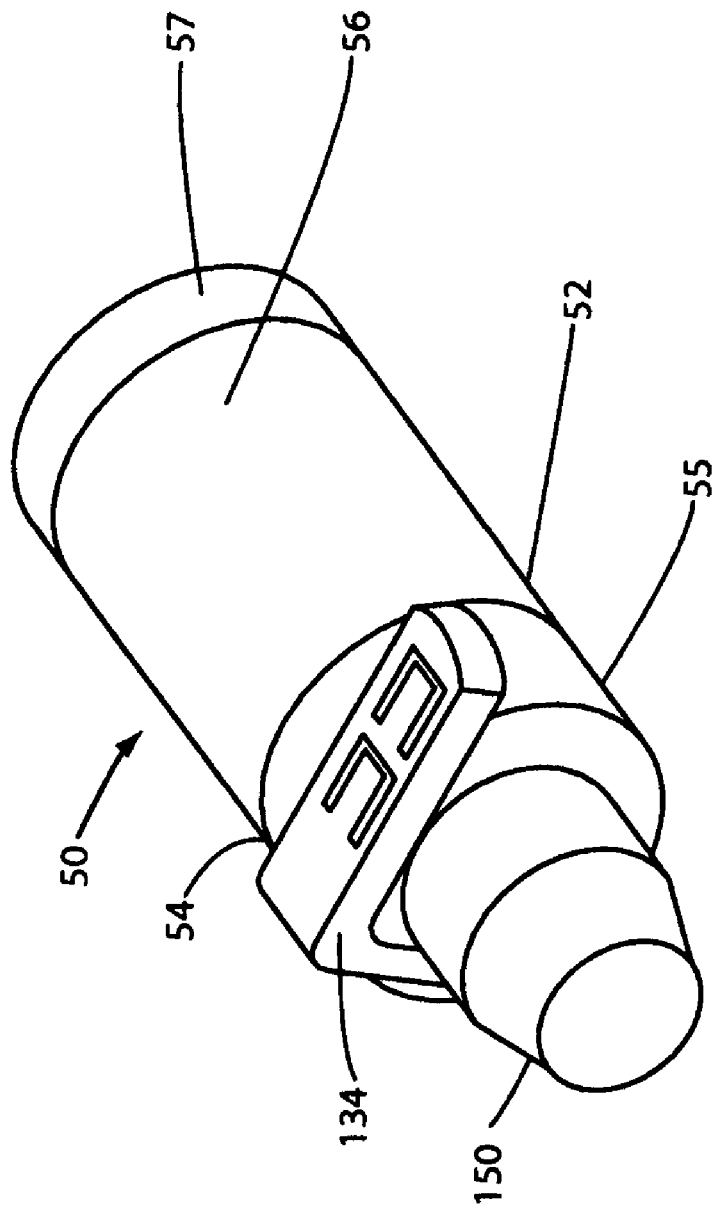
FIG. 1 is a generally perspective, top view of one form of the fluid dispensing apparatus of the present invention for dispensing medicaments to a patient.

As used herein, the following terms have the following meanings:

Unitary Container
A closed container formed from a single component.

Continuous/Uninterrupted Wall
A wall having no break in uniformity or continuity.

Patient
Individual seeking medical care.

Hermetically Sealed Container
A container that is designed and intended to be secure against the entry of microorganisms and to maintain the safety and quality of its contents after pressurizing.

Biologic
A virus, therapeutic serum, toxin, antitoxin, vaccine, blood, blood component or derivative, allergenic product, or analogous product applicable to the prevention, treatment or cure of diseases or injuries of man.

Drug
As defined by the Food, Drug and Cosmetic Act, "drugs" are "articles (other than food) intended for the use in the diagnosis, cure, mitigation, treatment, or prevention of disease in man or other animals, or to affect the structure or any function."

Drug Product
A finished dosage form (e.g. tablet, capsule, or solution) that contains the active drug ingredient usually combined with inactive ingredients.

Artificial Blood Substitutes

Blood Substitutes are used to fill fluid volume and/or carry oxygen and other gases in the cardiovascular system. These include volume expanders for inert products, and oxygen therapeutics for oxygen-carrying products.

Resuscitation Fluids

Infusion of hyperosmotic-hyperoncotic solutions such as hypertonic saline dextran (HSD) as used for resuscitation of traumatic shock and perioperative volume support or as an adjunct to other conventional isotonic crystalloid solutions. Where hypotension is caused by myocardial depression, pathological vasodilatation and extravascation of circulating volume due to widespread capillary leak, a resuscitative effort is attempted to correct the absolute and relative hypovolemia by refilling the vascular tree. Here resuscitation with a small volume of hypertonic-hyperoncotic solution allows systemic and splanchnic hemodynamic and oxygen transport recovery, without an increase in pulmonary artery pressure. Alternate types of normotonic, hyperoncotic, hypertonic, and hyper-tonic-hyperoncotic solutions can be used for systemic hemodynamic recovery.

KVO

KVO—"keeping-the-vein-open" in an IV set-up, a phrase that refers to the flow rate of a maintenance IV line established as a prophylactic access.

Nutritionals

Dietary supplemental enteral nutrition support feeding solutions used for nasoenteric application typically used in nasogastric, nasoduodenal and nasojejunal or intravenous routes of administration.

Beneficial Agent

The term "beneficial agent" can include any substance or compound that is biologically active and includes any physiologically or pharmacologically active substance that produces a localized or systemic effect in humans or animals and that can be delivered by the present invention to produce a beneficial and useful result.

Diluent

A liquid that dilutes, as in an inert solution used to dilute a medicament. An inert liquid carrier of a beneficial agent.

Device

An instrument, apparatus, implement, machine, contrivance, implant, in vitro reagent, or other similar or related article, including any component, part or accessory, which is intended for use in the diagnosis, cure, treatment or prevention of disease. A device does not achieve its intended purpose through chemical action in the body and is not dependent upon being metabolized to achieve its purpose.

Apparatus

An appliance or device for a particular purpose: An integrated group of materials or apparatus used for a particular purpose. The totality of means by which a designated function is performed or a specific task executed, a group of body parts that work together to perform a given function.

Reservoir

A receptacle or chamber for storing a fluid. A part of a machine, apparatus, where liquid is stored.

Liquid Container

A receptacle for holding a liquid. A fluid dispenser that is carried or transported.

Collapsible

To cause to fold, break down, or fall down or inward or as in bent-over or doubled-up so that one part lies on another.

Collapsible Container

A dispensing apparatus in which one or more walls of the container are made of a material which will deform (collapse) when pressure is applied thereto; or a dispensing apparatus having a collapsible or telescoping wall structure.

Aseptic Processing

The term "aseptic processing" as it is applied in the pharmaceutical industry refers to the assembly of sterilized components and product in a specialized clean environment.

Sterile Product

A sterile product is one that is free from all living organisms, whether in a vegetative or spore state.

Blow-Fill-Seal Process

The concept of aseptic blow-fill-seal (BFS) is that a container is formed, filled, and sealed as a unitary container in a continuous manner without human intervention in a sterile, enclosed area inside a machine. In the process multi-stepped, pharmaceutical grade resin is extruded into a tube, which is then formed into a container. A mandrel is inserted into the newly formed container and filled. The container is then sealed, all inside a sterile, shrouded chamber. The product is then discharged to a non-sterile area for packaging and distribution.

Integrally Formed

An article of one-piece construction, or several parts that are rigidly secured together and is smoothly continuous in form and that any such components making up the part have been then rendered inseparable.

Septum

A word borrowed from the Latin "saeptum" meaning a dividing wall or enclosure; thus, a thin partition or membrane that divides two spaces.

Slit Septum

A septum that is partially slit to aid in cannula penetration.

Penetrating

Tending to penetrate; having the power of entering or piercing.

Cutting

Capable of or designed for incising, shearing, or severing as to cut off from a main body.

Frangible

An article, item or object that is capable of being ruptured or broken, but does not necessarily imply any inherent materials weakness. A material object, under load that demonstrates a mechanical strain rate deformation behavior, leading to disintegration.

Luer Lock Connector

A connector used to connect medical apparatus. Classically, the Luer consists of a tapered barrel and a conical male part that fits into it with or without a seal.

Surface Treatment

The processes of surface treatments, more formally surface engineering, to tailor the surfaces of engineering materials to change, alter or modify the physical surface characteristics and improve the function of the materials properties for its intended purpose.

Spring

A mechanical element that can be deformed by a mechanical force such that the deformation is directly proportional to the force or torque applied to it. An elastic machine component able to deflect under load in a prescribed manner and to recover its initial shape when unloaded. The combination of force and displacement in a deflected spring is energy which may be stored when moving loads are being arrested.

Constant Force Spring

Constant force springs are a special variety of extension spring. They are tightly coiled wound bands of pre-hardened spring steel or stainless steel strip with built-in curvature so that each turn of the strip wraps tightly on its inner neighbor. When the strip is extended (deflected) the inherent stress resists the loading force, the same as a common extension spring, but at a nearly constant (zero) rate. The constant-force spring is well suited to long extensions with no load build-up. In use, the spring is usually mounted with the ID tightly wrapped on a drum and the free end attached to the loading force. Considerable flexibility is possible with constant-force springs because the load capacity can be multiplied by using two or more strips in tandem, or back-to-back. Constant force springs are available in a wide variety of sizes.

Figure 2:
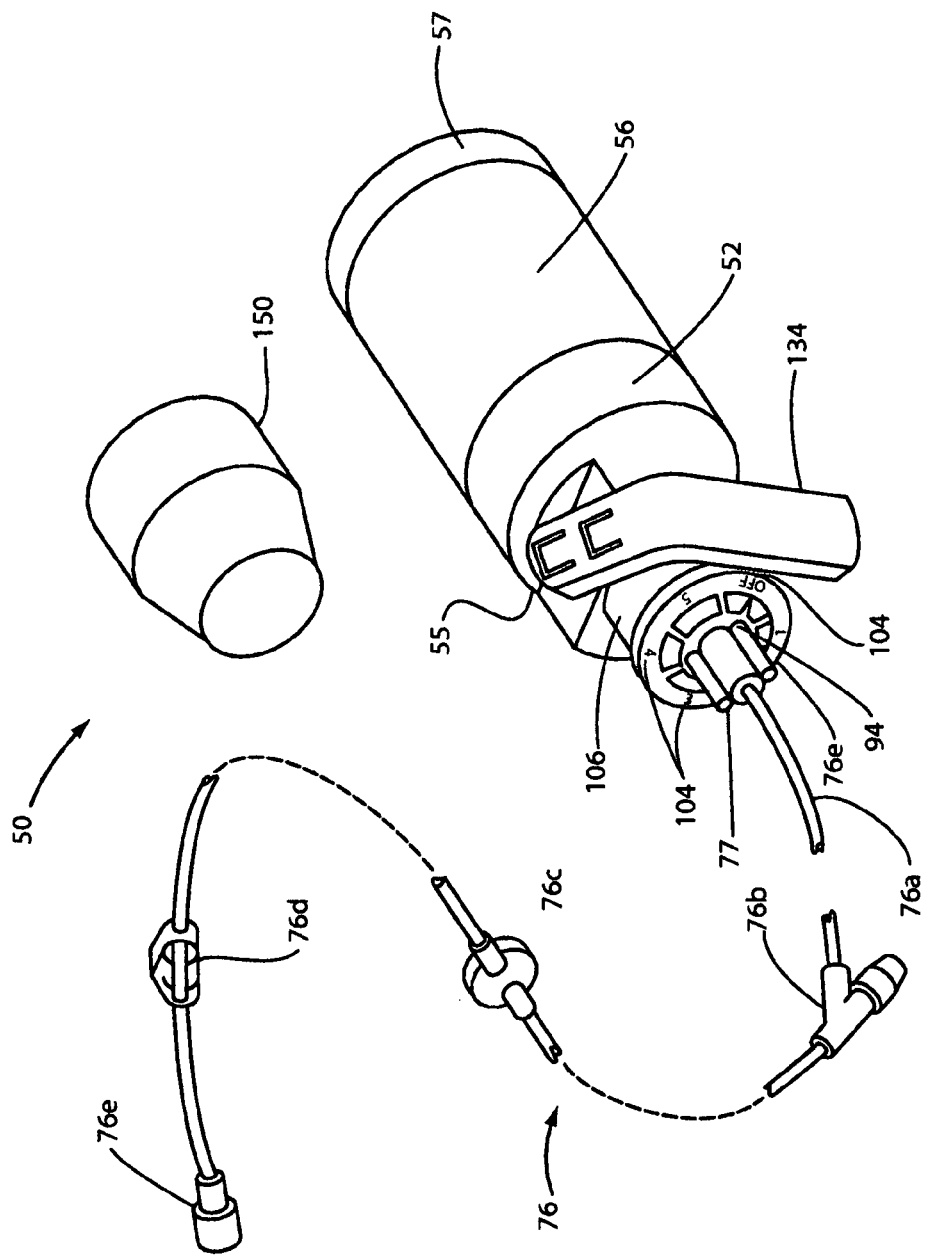
FIG. 2 is a generally perspective, exploded view of the fluid dispensing apparatus shown in FIG. 1 as it appears with a top cover of the device removed.

Referring to the drawings and particularly to FIGS. 1 through 3, one form of the fluid dispensing apparatus of the present invention for dispensing medicaments to a patient is there shown and generally designated by the numeral 50. The dispensing apparatus here comprises a supporting structure 52, which includes a housing 54 having an upper portion 55 and a generally cylindrically shaped skirt portion 56. Supporting structure 52 can be constructed from metal, plastic or any suitable material. Connected to portion 56 is a base segment 57, the details of construction of which will presently be described.

Figures 4A, 4B:
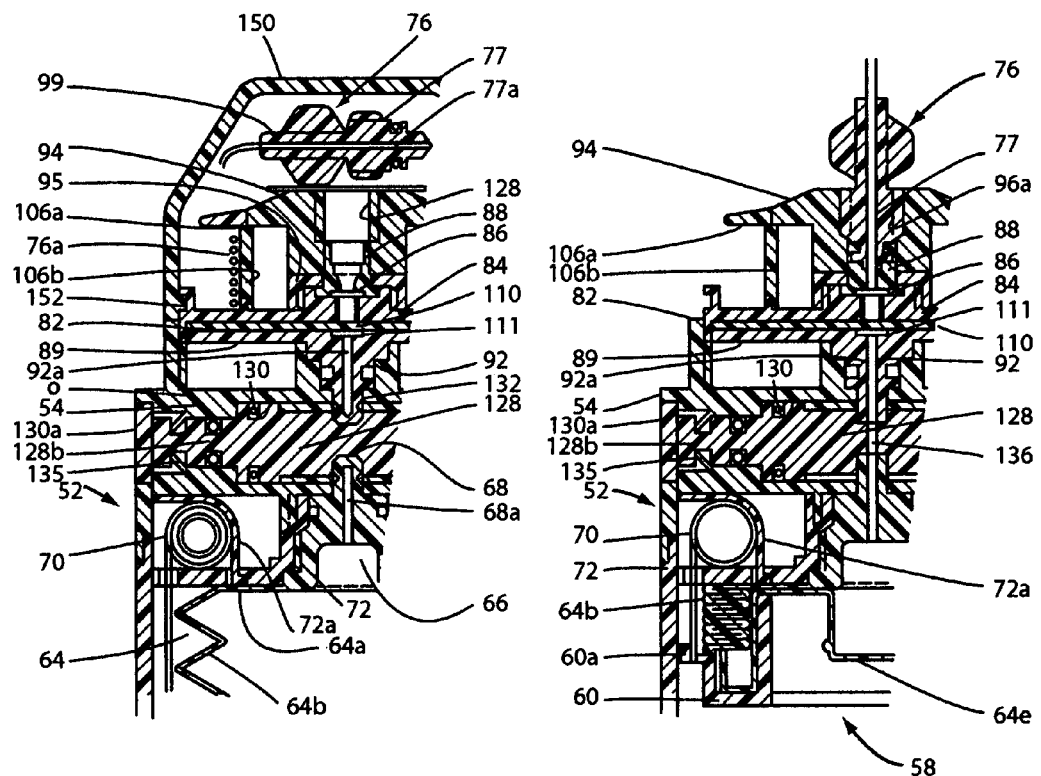
FIG. 4A is an enlarged, fragmentary, longitudinal, cross-sectional view of the left-hand portion of the apparatus shown in FIG. 3.
FIG. 4B is a fragmentary, longitudinal, cross-sectional view, similar to FIG. 4A, but showing the various components of the apparatus as they appear following delivery to the patient of the fluid contained within the device reservoir.

Disposed within skirt portion 56 is a carriage assembly 58, which is movable between a first position shown in FIGS. 3 and 4A and a second position shown in FIG. 4B. As best seen by referring to FIGS. 4A and 4B, carriage assembly 58 comprises a carriage 60 having a carriage flange 60a to which the novel stored energy means of the present invention is operably interconnected. Carriage assembly 58 is releasably locked in its first position by a novel locking means the character of which will be described in the paragraphs, which follow.

Carried by carriage assembly 58 is a reservoir defining assembly 64 that defines a fluid reservoir 65. As illustrated in FIGS. 3 and 6, reservoir defining assembly 64 includes a top wall 64a, an accordion-like side wall 64b that is connected to top wall 64a and a bottom wall 64c that is connected to side wall 64b. As illustrated in FIG. 3, bottom wall 64c includes a cup-shaped portion 64e. Reservoir 65 has a combination inlet/outlet 66 that is formed in a reservoir nipple 68 showing a score-line 69 that also comprises a part of the reservoir assembly 64.

In the preferred form of the invention shown in FIG. 6, nipple 68 is sealably interconnected with top wall 64a in accordance with an aseptic blow-fill-seal technique of a character well understood by those skilled in the art. This blow-fill-seal technique comprises the continuous extrusion through an extruder head of a length of a parison in the form of a hollow tube between and through two co-acting first or main mold halves. The method includes the step of cutting off the parison below the extruder head and above the main mold halves to create an opening which allows a blowing and filling nozzle assembly to be moved downwardly into the opening in the parison for molding and thereafter filling a molded container.

When the container portion of the container assembly is filled with the desired amount of liquid, the blowing and filling nozzle assembly is retracted from the opening in the parison. A separate pair of co-acting second or upper sealing mold halves are then moved together around the exposed length of parison to form and seal the container upper portion. The finished container assembly, completely formed, filled, and sealed as a unitary structure is then conveyed out of the molding apparatus. Further information concerning aseptic blow-fill and blow-fill-seal techniques is available from Weiler Engineering of Elgin, Illinois and from Rommelag of Waiblingen, Germany.

Figure 8:
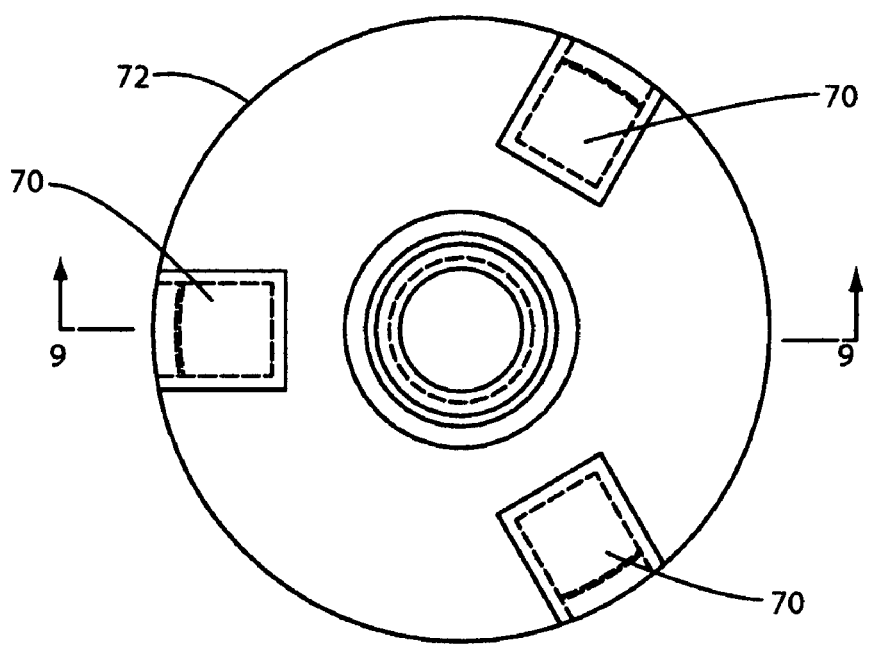
FIG. 8 is a cross-sectional view taken along lines 8-8 of FIG. 3.
Figure 9:
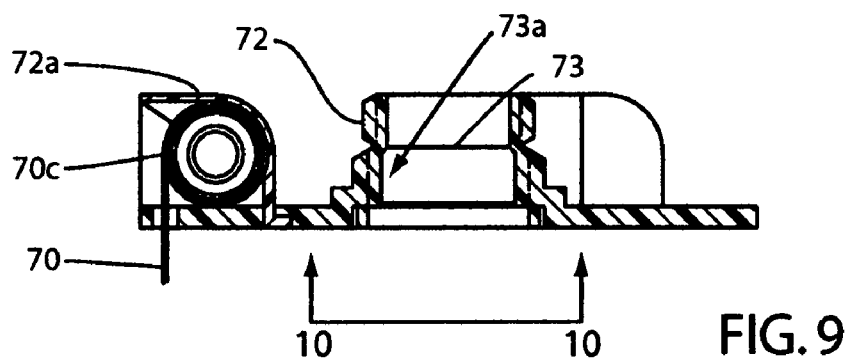
FIG. 9 is a cross-sectional view taken along lines 9-9 of FIG. 8.
Figure 10:
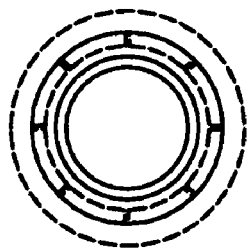
FIG. 10 is a view taken along lines 10-10 of FIG. 9.
Figure 11:
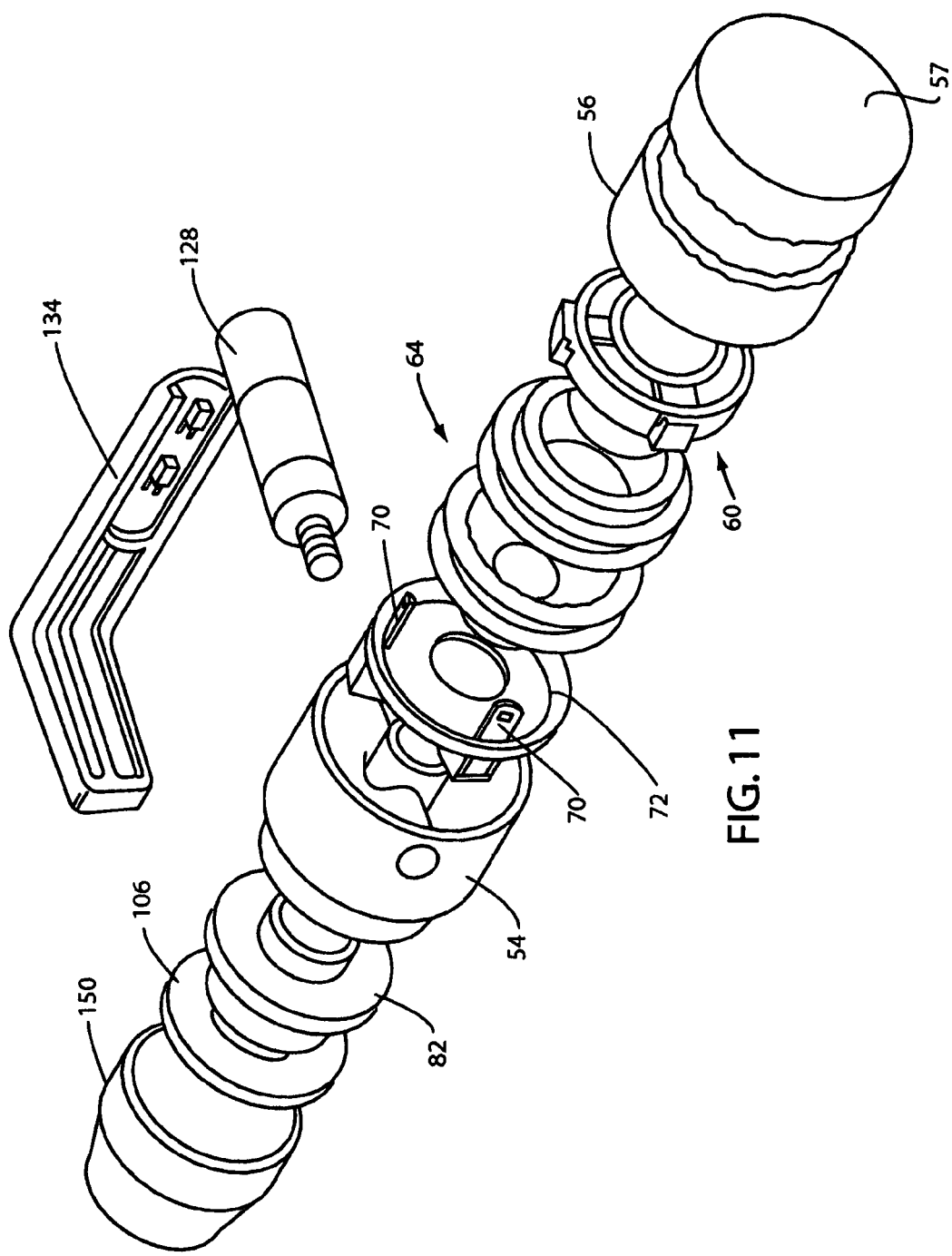
FIG. 11 is a generally perspective, exploded view of the fluid delivery apparatus illustrated in FIG. 1.

To controllably move the carriage assembly from its first position to its second position and to thereby controllably expel the fluid from the fluid reservoir 65, novel stored energy means are provided. These novel stored energy means, which are operably associated with carriage assembly 58, are here provided in the form of three circumferentially spaced-apart, constant force springs 70 (FIGS. 3 and 8). It is to be understood that an alternate number of springs can be used as may be desired. As illustrated in FIGS. 3, 8 and 9, constant force springs 70 are housed within spring retainers 72a which form a part of a spring housing 72 which includes a cavity 73 having internal threads 73a. Housing 72, in turn, forms a part of the supporting structure 52 of the apparatus. The details of construction and operation of these important constant force springs will presently be described.

As will be discussed more fully in the paragraphs which follow during the fluid dispensing step, as the carriage assembly 58 is moved by the constant force springs 70 toward its deployed position, the accordion-like sidewall 64b of the reservoir assembly 64 will be urged to move into the collapsed configuration shown in FIG. 4B and in so doing will cause the fluid contained within the container to be controllably and substantially expelled therefrom.

To further control the flow of fluid from reservoir 65 toward the administration set 76 of the invention and then on to the patient, novel fluid flow control means are provided. The fluid flow control means, which is carried by the supporting structure 52, here comprises two cooperating components, namely a rate control means for controlling the rate of fluid flow from the collapsible reservoir toward the administration set and an operating means for controlling fluid flow between the collapsible reservoir and the rate control means.

Considering first the rate control means of the invention, this important means comprises a rate control housing 82, which includes a first cover member 84, that engages a selector element 86 which is received within a cavity 87 provided in selector member 88 and located therewithin by a flat "F" (FIG. 23). Selector member 88, which has an enlarged diameter portion 88a (See FIG. 14), forms a part of the selector means of the invention for selecting the desired rate of fluid flow from the fluid reservoir toward the administration set. Cover member 84 also has a rate control plate cavity 84b. As best seen in FIGS. 13 and 14, rate control housing 82 includes a second cover member 89 having an outwardly extending attached nipple 92, the purpose of which will presently be described.

Figure 12:
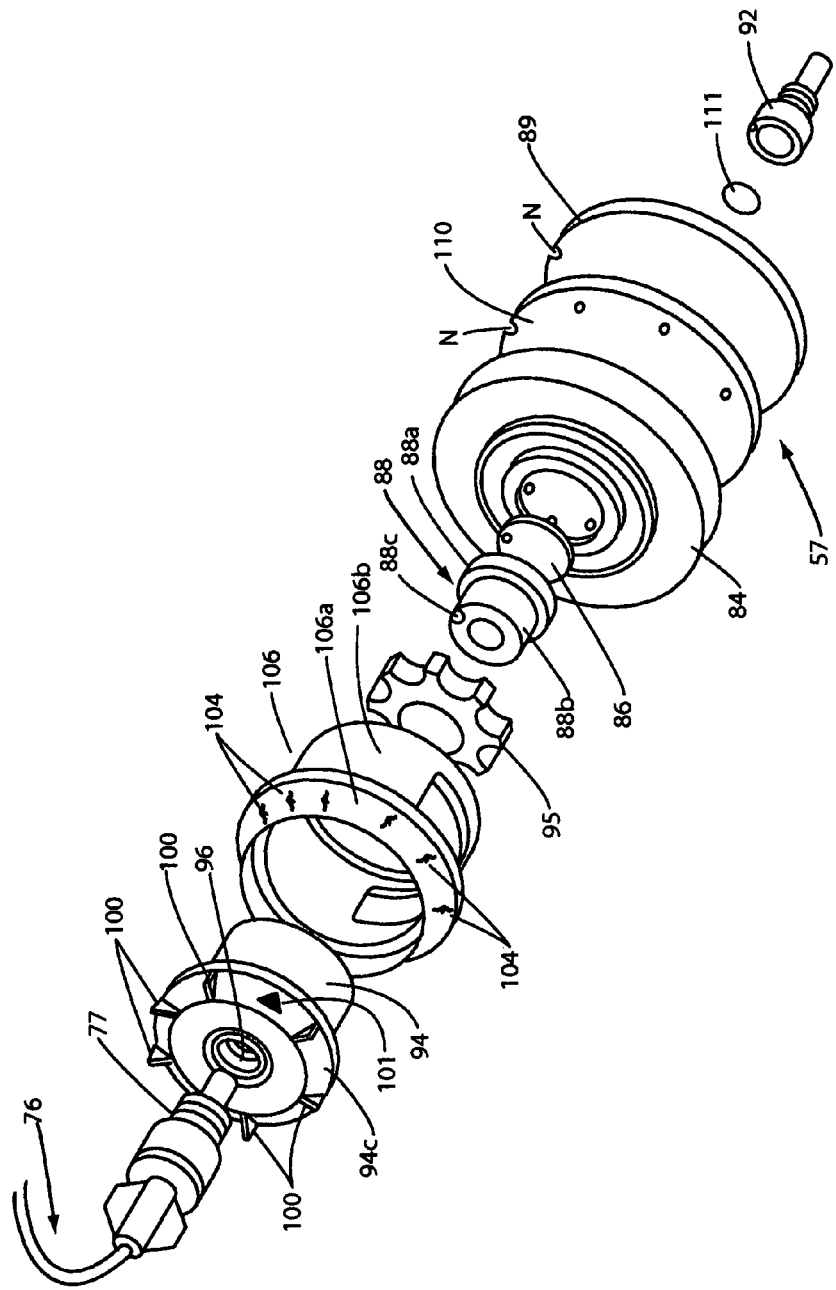
FIG. 12 is a generally perspective, exploded view of the multiple flow rate control assembly of the apparatus of the invention and a portion of the administration set.

Interconnected with rate control housing 82 is a selector knob 94, that includes a central bore 96, the enlarged, threaded diameter portion 96a of which sealably receives the connector hub 77 of the administration set 76 (FIG. 12). The enlarged diameter portion 96b of bore 96, which includes a groove 96c, receives the reduced-diameter portion 88b of selector member 88 (FIGS. 13 and 14). A threaded cap 95 retains selector member 88 in position. As shown in FIG. 14, selector member 88 includes an orientation spine 88s that is received in groove 96c. Selector knob 94 also includes an outwardly extending flange 94c which carries circumferentially spaced finger-gripping elements 100 which assist in rotating the selector knob (FIG. 12). Flange 94c also carries an indicator arrow 101, which, upon rotation of the selector member, aligns with flow rate indicia 104 imprinted on the rim portion 106a of a selector member support 106 that supports selector knob 94 (FIGS. 2, 12 and 13). Selector member support 106 also includes a skirt portion 106b that is interconnected with rate control housing 82 in the manner shown in FIGS. 3 and 13. It is to be noted that the movable components of the dispensing apparatus typically carry conventional O-rings to provide appropriate sealing of the components within the apparatus with their mating parts. Throughout the drawings these O-rings are identified as "O".

Figure 26:
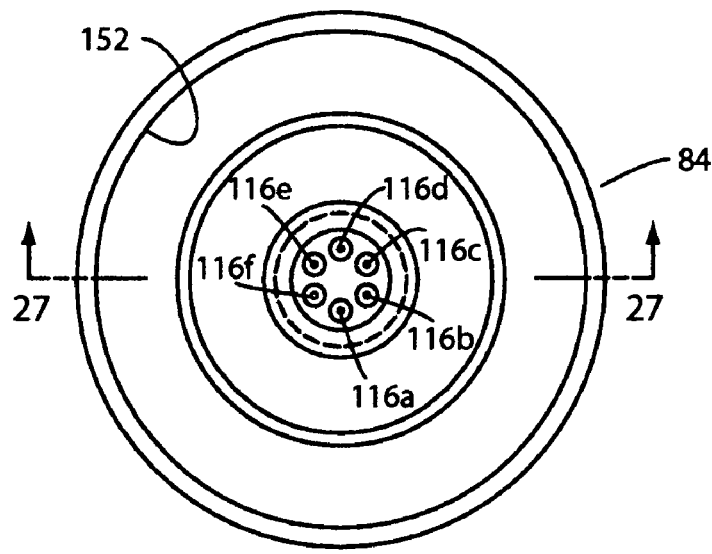
FIG. 26 is a top plan view of the other of the rate control covers.
Figure 27:
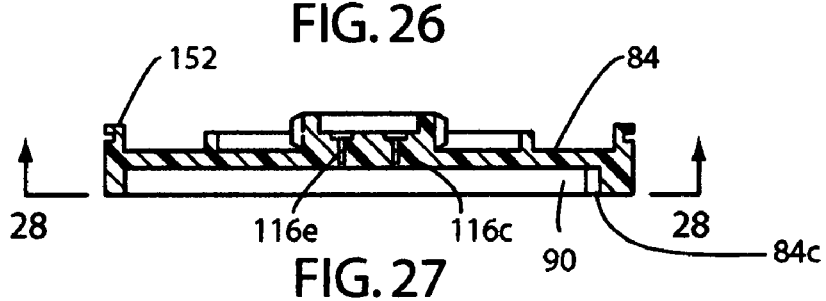
FIG. 27 is a cross-sectional view taken along lines 27-27 of FIG. 26.
Figure 28:
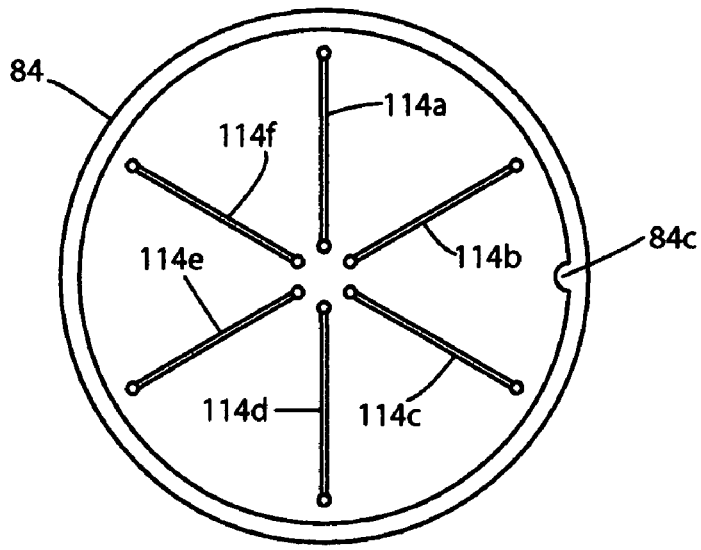
FIG. 28 is a view taken along lines 28-28 of FIG. 27.
Figure 35:
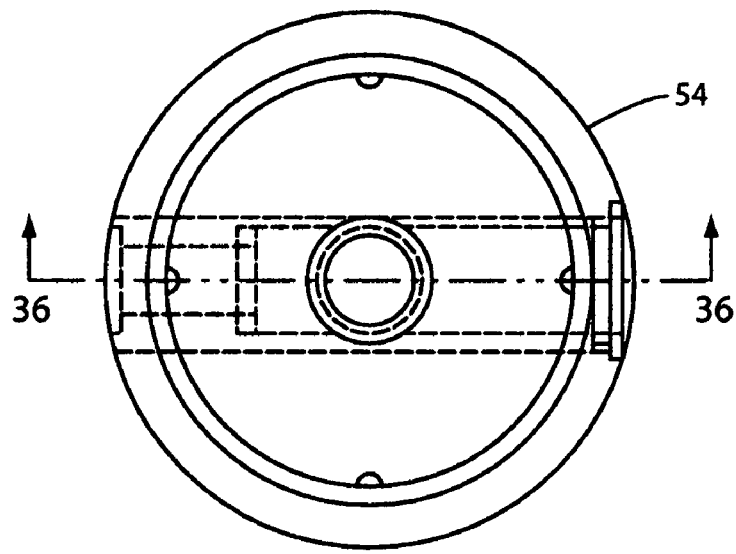
FIG. 35 is a top plan view of a portion of the supporting structure of the apparatus of the invention.

As illustrated in FIGS. 4A and 4B, first cover member 84 cooperates with second cover 89 to sealably enclose the rate control plate 110 of the invention (FIGS. 13 and 14) that is disposed between covers 84 and 89 and is oriented therebetween by a spline 84c on cover 84 and notches "N" formed on cover 89 and plate 110. Rate control plate 110 is provided with a plurality of fluid flow channels of different lengths, widths, depths and geometry (FIG. 32) that are in fluid communication with outlet 66 of collapsible reservoir 65 via the operating means of the invention, central passageway 92a of nipple 92, and central passageway 68a of nipple 68. After operating the operating means of the invention in a manner presently to be described to permit fluid to flow into the passageway of the nipples 68 and 92 via the operating means, fluid will flow through passageway 89a, through a conventional particulate filter 111, into a well 89b and into inlet 110a of the rate control plate. From inlet 110a, the fluid will flow into the various circuitous fluid channels 112a, 112b, 112c, 112d, 112e and 112f formed in the rate control plate, each of which is of a different length, width, depth and geometry (see FIGS. 12 and 32). As each of the channels fills with the medicinal fluid to be dispensed to the patient, the fluid will flow into outlet passageways 114a, 114b, 114c, 114d, 114e and 114f respectively formed in rate control cover 84 (FIG. 28). From these outlet passageways, the fluid will flow into and fill circumferentially spaced-apart fluid passageways 116a, 116b, 116c, 116d, 116e and 116f formed in cover member 84 (see FIGS. 26 and 27).

As best seen by referring to FIG. 21, selector member 88, which controllably rotates with knob 94, is provided with an inlet 120, a radially extending inlet passageway 122 and an outlet 124 that is in communication with a central passageway 126 via an orifice 86a of the selector element 86 (FIG. 23). When the connector hub 77 of the administration set 76 is in position within the cavity 96a formed in selector knob 94 in the manner shown in FIG. 4B, the fluid will flow through the selector film 86 and directly into the inlet 77a of the hub 77 of the administration set 76 (FIGS. 3, 20, 21, 22, and 23).

With the construction just described, by rotating the selector knob 94, (See FIG. 4B) which, in turn, rotates selector member 88, inlet 120 of the selector member can be selectively brought into index with one of the axially extending passageways formed in selector member 88, thereby providing fluid communication with a selected one of the circuitous flow passageways formed in rate control plate 110. Since outlet passageway 124 is in fluid communication with the administration set 76 in the manner previously described, the rate of fluid flow toward the patient can be precisely controlled by selecting a rate control passageway of appropriate length that is formed in rate control plate 110.

Figure 36:
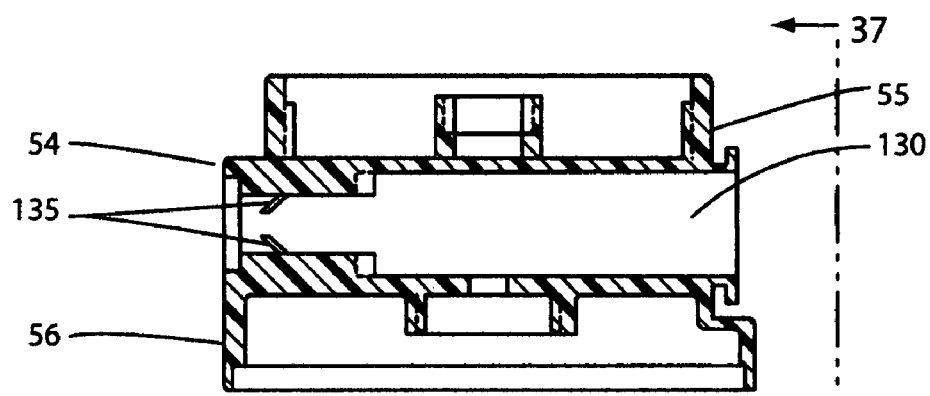
FIG. 36 is a cross-sectional view taken along lines 36-36 of FIG. 35.
Figure 37:
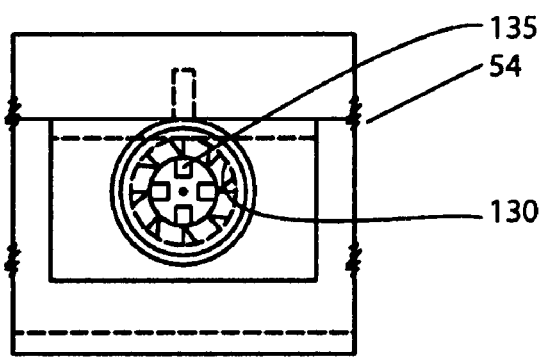
FIG. 37 is a view taken along lines 37-37 of FIG. 36.

Considering now the previously identified operating means of the invention, this important means, which controls fluid flow between collapsible reservoir 65 and passageway 92a of nipple 92 of the rate control means, here comprises an operating shaft 128 (FIGS. 4A, 4B and 38) that is sealably, rotatably mounted within a generally cylindrical-shaped chamber 130 (FIGS. 4A, 4B and 36) formed in housing 54 of supporting structure 52 (FIGS. 3, 4A and 36). Operating shaft 128 can be rotated within chamber 130, which is closed by a closure cap 130a, by an "L"-shaped operating handle 134 (FIG. 2) between the position shown in FIG. 44, blocking fluid flow from collapsible reservoir 65 toward administration set 76 and the position shown in FIG. 46 permitting fluid flow from the reservoir toward the administration set.

Turning particularly to FIGS. 38 through 41, operating shaft 128 can be seen to comprise a body portion 128a and a reduced-diameter neck portion 128b. Circumferentially spaced-apart, generally arcuate-shaped cavities 131 and 132, which are formed in body portion 128a, are strategically located to receive the end portions of nipples 68 and 92 when the operating shaft is held in position within chamber 130 by integral retainer clips 135 in the manner shown in FIG. 36. Also formed within operating shaft 128 is a transversely extending fluid passageway 136, which, upon rotation of the operating shaft by handle 134, can be moved into alignment with the fluid passageways 68a and 92a of nipples 68 and 92 respectively (see FIG. 46).

Mounted within each of the cavities 131 and 132 is a spring knife 140, which, as indicated in FIGS. 41 and 42, includes a cutting edge 140a formed proximate one extremity and a pair of mounting clips 142 provided proximate the opposite extremity. Tabs 142a of the mounting clips are received within slots 144 formed in body portion 128a so as to secure the spring knives within the arcuate cavities in the manner illustrated in FIG. 44. With this construction, as the operating shaft 128 is rotated by handle 134 from the position shown in FIG. 44 into the position shown in FIG. 45 the spring knives will cleanly sever the sealed tip portions 68b and 92b of nipples 68 and 92 respectively. Continued rotation of operating member 128 will move sealed tip portions 68b and 92b into the cavities for rotation therewith (FIG. 45) and will move transverse passageway 136 into alignment with passageways 68a and 92a in a manner shown in FIG. 46. With the operating member in this position fluid can flow freely from reservoir 65 toward the rate control means of the invention via passageways 68a and 92a of nipples 68 and 92.

From passageway 68a, fluid will flow through passageway 136, through passageway 92a, through conventional particulate filter 111, through well 89b, through outlet 89a, into inlet 110a of rate control plate 110 of the rate control assembly and then into the various circuitous fluid channels 112a, 112b, 112c, 112d, 112e and 112f formed in the rate control plate (see FIGS. 3, 13 and 32). Rate control plate 110, which can be constructed from various plastics, is oriented relative to members 84 and 89 by the previously identified notches "N" and spines "S" and 84c. Filter 111 is maintained in position within cavity 92b of member 92 which is received in a cavity 89b formed in plate 89. As each of the channels fills with the medicinal fluid to be dispensed to the patient, the fluid will flow next into outlet passageways 114a, 114b, 114c, 114d, 114e and 114f respectively formed in rate control cover 84 (FIG. 28). From these outlet passageways, the fluid flows into and fills circumferentially spaced-apart fluid passageways 116a, 116b, 116c, 116d, 116e and 116f formed in cover member 84 (see FIGS. 26 and 27). By controllably rotating knob 94 which in turn rotates the selector member 88, inlet 120 thereof can be selectively brought into index with one of the fluid passageways formed in cover member 84 via element 86, thereby providing fluid communication with a selected one of the circuitous flow passageways formed in rate control plate 110. Since outlet passageway 124 of the selector member 88 is in fluid communication with the administration set 76 in the manner previously described the fluid can be delivered to the patient at a selected controlled rate of flow.

With the apparatus in the configuration shown in FIG. 1 and with the fluid reservoir 65 filled with the medicament to be dispensed to the patient, the dispensing operation can be commenced by removing the top cover 150 which is snapped over a cover connector 152 that protrudes from the rate control cover 84. With the top cover removed, the administration line 76a of the administration set 76 can be unwrapped from the sleeve 106b of the selector knob support 106 about which it has been coiled (see FIG. 3). Removal of the top cover 150 also exposes the selector knob 94 so that the fluid flow rate can be selected by rotating the selector knob to the desired flow rate indicated by the indicia 104 imprinted on the rim of the selector knob support 106 (FIG. 2). In this regard, it is to be noted that selector knob 94 is provided with a plurality of circumferentially spaced cavities 97c (FIG. 17) that are engaged by a protuberance 106p formed on inwardly extending flange 106d of support 106 (FIGS. 13 and 31). With the desired flow rate thusly set, the operating shaft 128 is next rotated through the use of the operating handle 134 from the starting position shown in FIG. 47 to the fully rotated position shown in FIG. 49. In this way, communication is opened between the reservoir outlet 66 and passageway 92a of nipple 92 which, in turn, is in communication with the rate control assembly of the invention.

Figure 51:
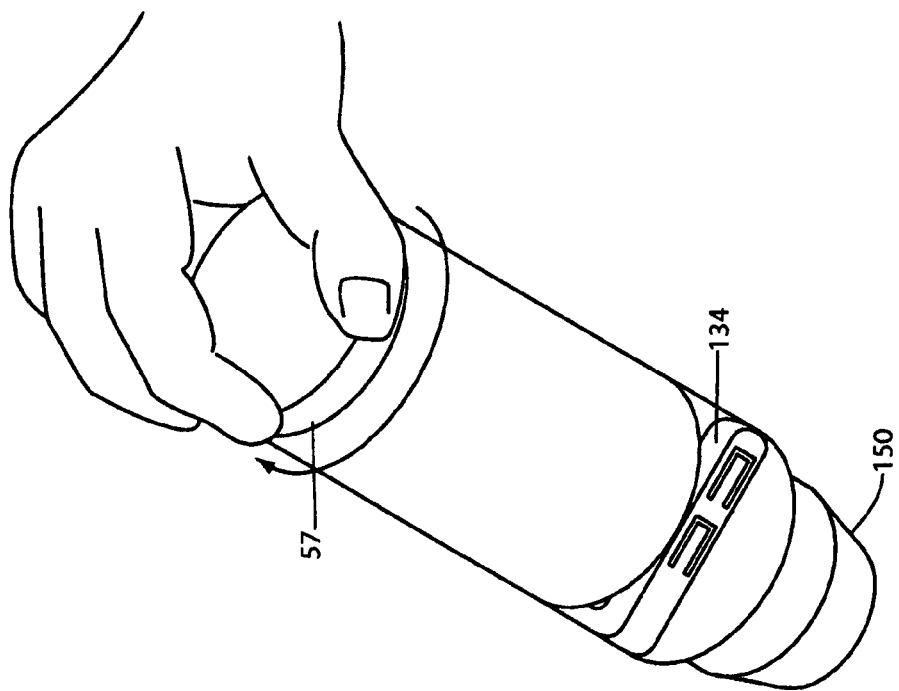
FIG. 51 is a generally perspective, diagrammatic view illustrating the operation of the locking means of the apparatus to release the carriage so as to arm the system to permit delivery of fluid to the patient via the administration set of the apparatus.
Figure 50:
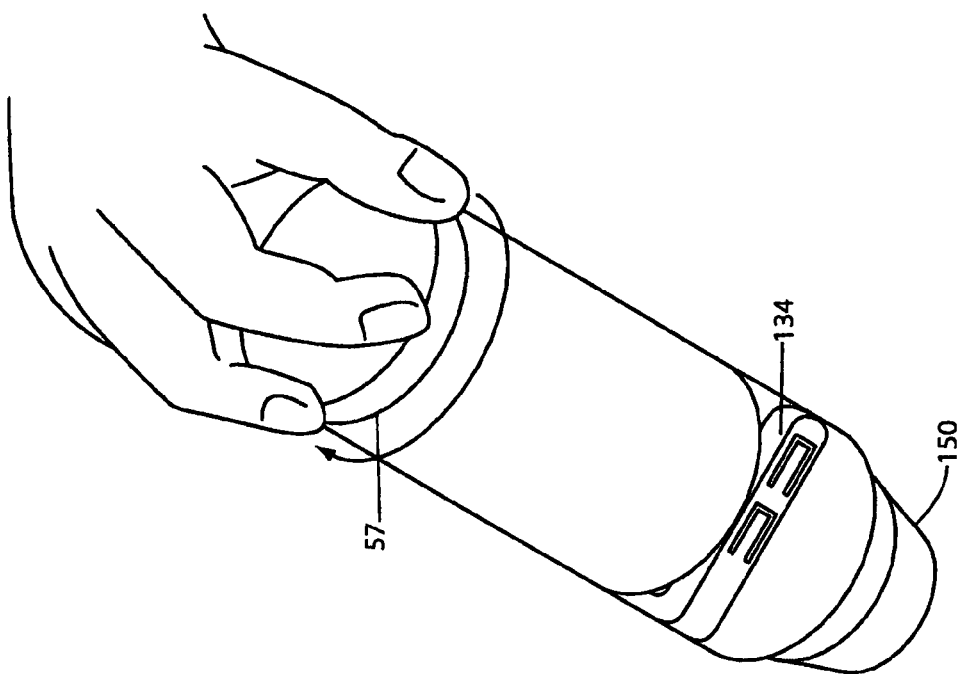
FIG. 50 is a generally perspective, diagrammatic view illustrating the operation of the locking means of the apparatus in a manner to lock the carriage to the base component of the apparatus structural support.

Following the controlled rotation of the operating shaft 128 in the manner shown in FIGS. 44 through 49, the carriage locking means of the invention can now be manipulated in the manner illustrated in FIG. 51 to release the carriage 60 from base segment 57 in order to permit the stored energy means, or constant force springs 70 to move the carriage from the fully deployed or extended starting position shown in FIG. 4A to the retracted position shown in FIG. 4B. In this regard, as best seen in FIGS. 4A, 4B and 51, the carriage locking means here comprises the previously identified base segment 57 which includes a locking sleeve 57a that is provided with a cam groove 155 that is adapted to mate with a male thread 157 formed on the base 57 of container 64 (see FIGS. 4A and 6). With this construction, upon rotating base segment 57 so as to release the carriage in the manner shown in FIGS. 4B and 51, carriage 60 is then free to move in response to the urging of the constant force springs 70 from the position shown in FIG. 4A to the fluid delivery position shown in FIG. 4B. As the carriage moves into the fluid delivery position the fluid contained within reservoir 65 will be caused to controllably flow toward reservoir outlet 66, into fluid passageway 68a of nipple 68, through passageway 136 formed in control member 128 and into passageway 92a of nipple 92. From passageway 92a, fluid will flow through conventional particulate filter 111, into the well 89b, through outlet 89a, and into inlet 110a of rate control plate 110 and then into the various circuitous fluid channels 112a, 112b, 112c, 112d, 112e and 112f formed in the rate control plate (see FIG. 32). As each of the channels fills with the medicinal fluid to be dispensed to the patient, the fluid will flow into and fill circumferentially spaced-apart fluid passageways 114a, 114b, 114c, 114d, 114e and 114f formed in cover member 84 (see FIG. 28). By controllably rotating the selector knob 94, inlet 120 of selector member 88 can be selectively brought into index with one of the fluid passageways 116a, 116b, 116c, 116d, 116e and 116f formed in cover member 84, thereby providing fluid communication with a selected one of the circuitous flow rate control passageways formed in rate control plate 110 and in this way select the desired rate of fluid flow to the administration set and then on to the patient.

In the present form of the invention, administration set 76, which comprises a part of the dispensing means of the invention for delivering medicinal fluids to the patient, includes, in addition to administration line 76a, a conventional "Y"-site injection septum or port 76b, a conventional gas vent and particulate filter 76c and a line clamp 76d. Provided at the distal end of the administration line is a Luer connector 76e of conventional construction (FIG. 2) which enables the apparatus to be interconnected with the patient in a conventional manner.

The stored energy members or constant-force springs 70, which are a special variety of extension spring, are readily commercially available from several sources, including Barnes Group Inc. of Bristol, Conn.; Stock Drive Products/Sterling Instrument of Hyde Park, N.Y. and Walker Corporation of Ontario, Calif. Constant force extension springs are basically high stress, long deflection apparatus that offer great advantages when used in applications, such as the present application, where very low or zero gradient is desired, where space is a factor and where very high reliability, accuracy, and linear force tolerance is required. Constant force springs, such as springs 70, provide markedly superior constant force loading when compared to conventional helical extension or like conventional types of springs. A constant force spring is typically a roll of pre-stressed metal strip that exerts a nearly constant restraining force to resist uncoiling or recoiling. The force is constant over time because the change in the radius of the curvature is constant. Springs 70 can be of a laminate construction, or alternatively spring 70 can comprise a single spring element of the character shown in the drawings.

Turning now to FIGS. 52 through 59, an alternate form of the dispensing apparatus of the present invention for dispensing medicaments to a patient is there shown and generally designated by the numeral 160. This alternate form of dispensing apparatus is similar in some respects to that shown in FIGS. 1 through 51 and like numerals are used in FIGS. 52 through 59 to identify like components. As before, the dispensing apparatus here includes a supporting structure 162 which includes an upper control portion 164 and a generally oval-shaped lower portion 166 that is interconnected with the upper portion in the manner best seen in FIG. 55 of the drawings.

The primary differences between this latest form of dispensing apparatus of the invention and that illustrated in FIGS. 1 through 51 and previously described herein reside in the provision of a pair of reservoir defining assemblies, or fluid containers that are housed within supporting structure 162 that is of a totally different construction and in the provision of totally differently configured stored energy means for acting on the reservoir defining assemblies.

Figure 59:
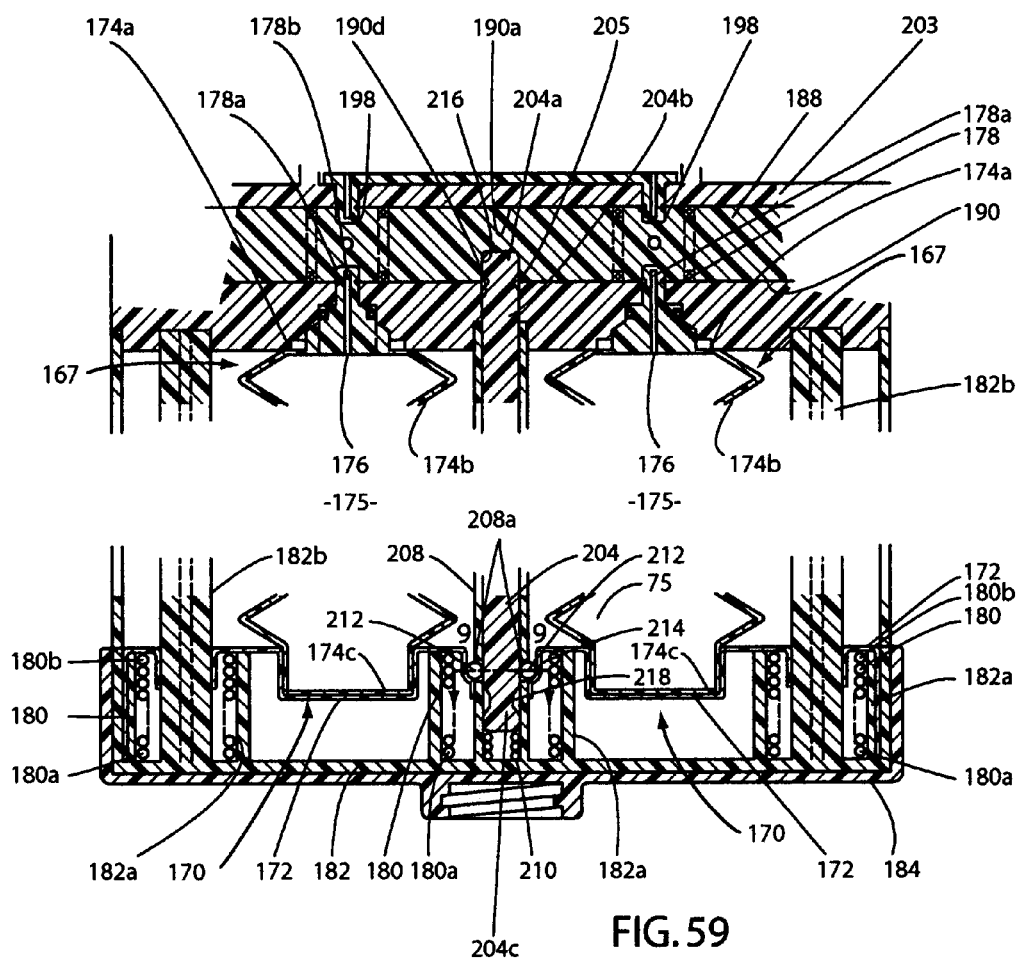
FIG. 59 is a fragmentary, cross-sectional view of the lower portion of the apparatus shown in FIG. 54.

Disposed within lower portion 166 of the supporting structure is a carriage assembly 170 that supports the reservoir defining assemblies 167 in the manner shown in FIG. 59. Carriage assembly 170 is movable between a first position shown in FIG. 59 and a second position shown in FIG. 61.

Figure 60:
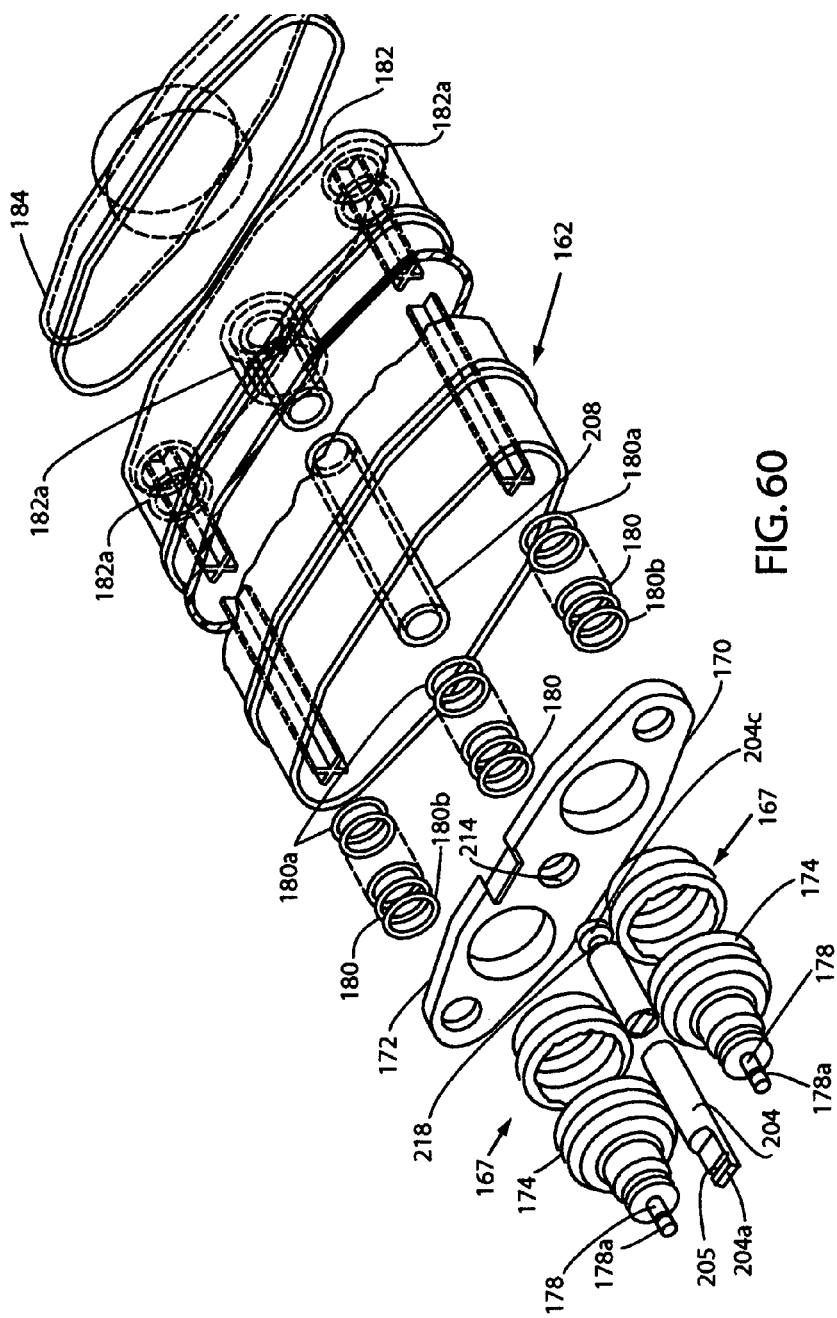
FIG. 60 is a generally perspective, exploded view of the portion of the apparatus illustrated in FIG. 59.

As best seen by referring to FIGS. 59 and 60, the carriage assembly 170 comprises a carriage 172 with which the novel stored energy means of the present invention is operably associated. The carriage assembly is releasably locked in its first lowered position by a novel locking means the character of which will be described in the paragraphs that follow.

Figure 64:
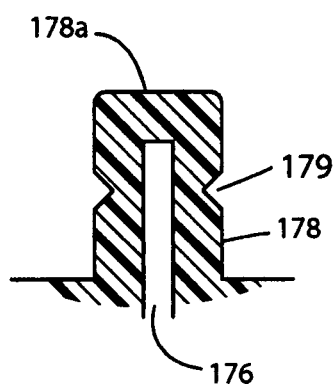
FIG. 64 is a greatly enlarged, cross-sectional view of the area designated in FIG. 63 as "64".
Figure 63:
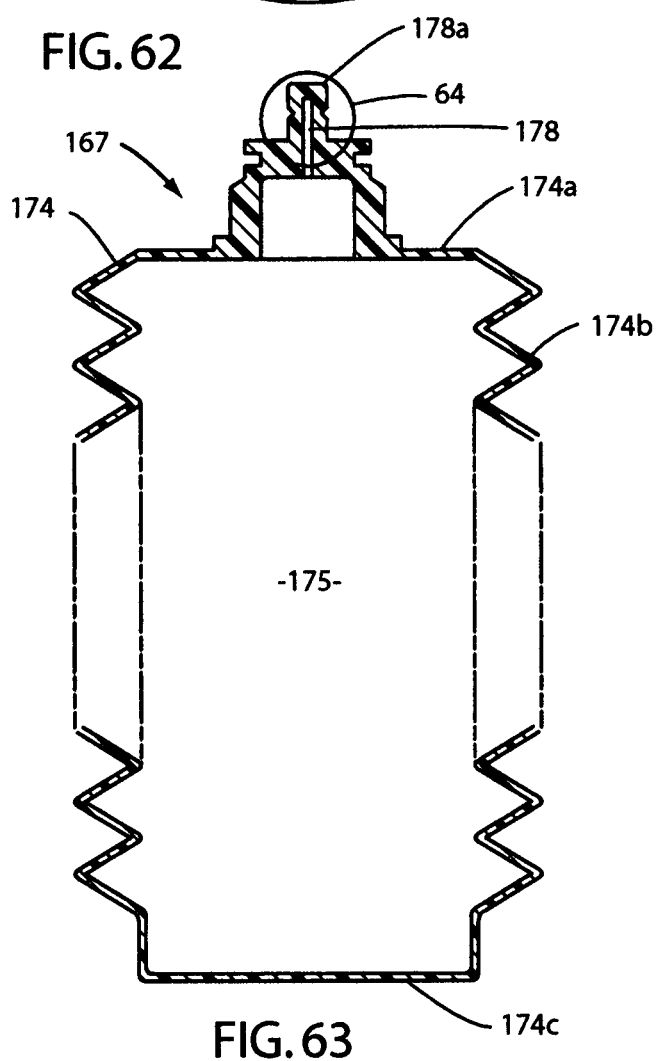
FIG. 63 is a cross-sectional view taken along lines 63-63 of FIG. 62.

The reservoir defining assemblies 167 are similar in construction to reservoir assembly 64 and each includes a sealed container 174 having a top wall 174a, an accordion-like side wall 174b that is connected to top wall 174a and a bottom wall 174c that is connected to a bellows-like side wall 174b (See FIG. 63). The sealed containers 174 of the preferred form of the invention as shown in FIG. 63 are formed in accordance with the previously described an aseptic blow-fill-seal technique. Each sealed container 174 defines a reservoir 175 that has a combination inlet/outlet 176 (FIG. 64). Combination inlet/outlet 176 is formed by a reservoir nipple 178 having a score-line 179. Reservoir nipple 178 also comprises a part of the reservoir defining assembly 167.

Figure 61:
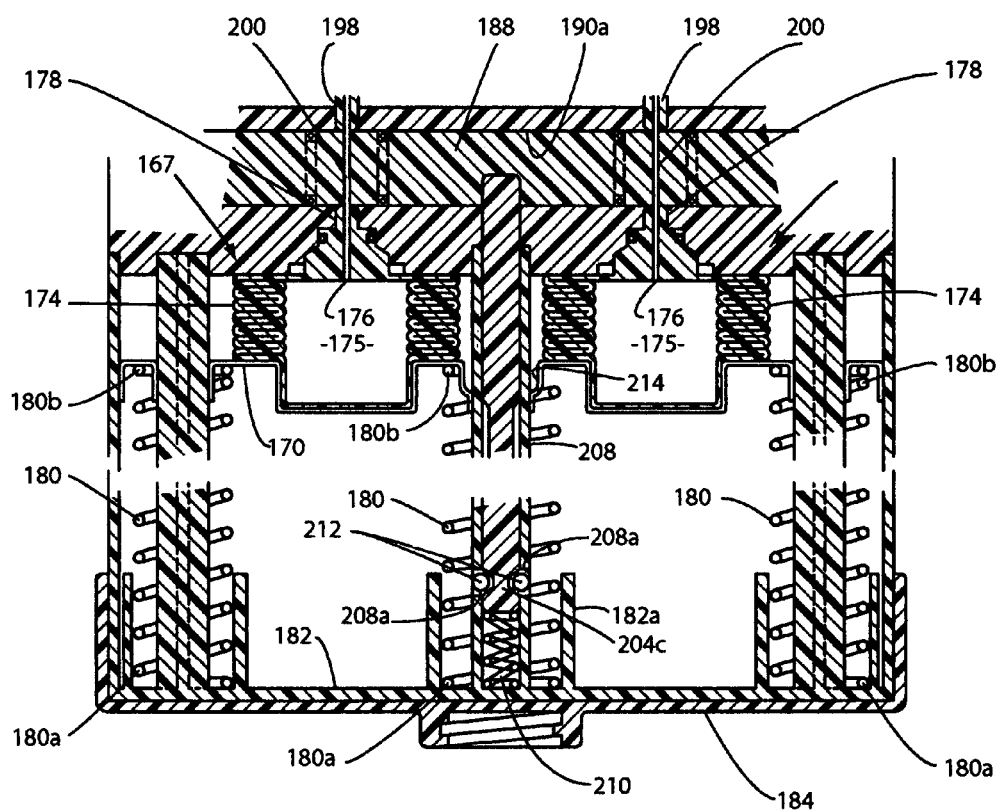
FIG. 61 is a view, similar to FIG. 59, but showing the configuration of the apparatus after the fluid in the fluid reservoirs of the apparatus has been dispensed to the patient.
Figure 62:
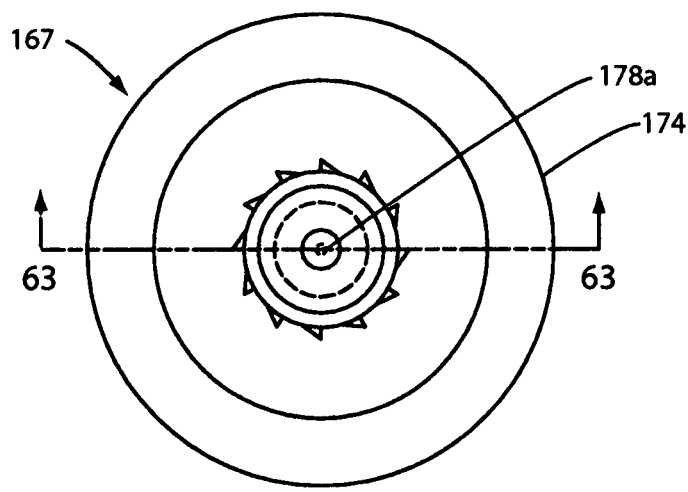
FIG. 62 is a top plan view of one of the fluid containers of the apparatus of the invention shown in FIG. 52.

To controllably move the carriage assembly 170 from its first position to its second position, novel stored energy means are provided. These novel stored energy means, which are operably associated with carriage assembly 170, are here provided in the form of three transversely spaced-apart coiled springs 180. As illustrated in FIGS. 59 and 61, one end 180a of each of the coil springs 180 is disposed in engagement with a generally oval-shaped support plate 182 that is carried by an end cap 184. Support plate 182 is provided with three transversely spaced-apart, generally cylindrically shaped, cup-like spring receiving portions 182a. The other end 180b of each of the coil springs 180 is disposed in engagement with carriage 172 (FIG. 59).

As indicated in FIG. 61, support 182 also includes guide means for guiding travel of the carriage assembly between the first position shown in FIG. 59 and the second position shown in FIG. 61. This guide means here comprises a pair of outwardly extending, spaced-apart guides 182b that function to guide the travel of carriage assembly 170 between its first and second positions. Also extending from support plate 182 is a centrally disposed locking shaft tube 208 the purpose of which will presently be described.

With the construction described in the preceding paragraphs, when the fluid reservoir is accessed by the reservoir accessing means of the invention and when the carriage locking means is manipulated in a manner presently to be described to unlock the carriage, coil springs 180 will move from their retracted position shown in FIG. 59 to their expanded position shown in FIG. 61, and in so doing will controllably move the carriage from its starting position shown in FIG. 59 to its fully deployed, or extended position shown in FIG. 61. Carriage assembly 170 is releasably locked in its first position by a novel locking means the character of which will presently be described.

As the carriage assembly moves toward its deployed position, the accordion sidewalls 174b of the containers 174 will move into their collapsed configuration shown in FIG. 61 and in so doing will cause the medicinal fluid contained within the containers to be controllably expelled therefrom.

To further control the flow of medicinal fluid from reservoirs 175 toward the administration set 76 of the invention and then on to the patient, flow control means are provided. As before this novel fluid flow control means, comprises two cooperating components, namely a rate control means for controlling the rate of fluid flow from the collapsible reservoirs to the patient and an operating means for controlling fluid flow between the collapsible reservoirs and the rate control means. The important operating means of this latest form of the invention here comprises an operating shaft 188 that is of a somewhat different construction that is rotatably mounted within a generally cylindrically shaped chamber 190a formed in reservoir cover member 190 that forms, a part of the upper control portion 164 of the supporting structure (FIGS. 55, 56, 57 and 58).

As before, operating shaft 188 can be rotated within chamber 190 by a generally "L"-shaped operating handle 191 between a first position blocking fluid flow from collapsible reservoirs 175 toward administration set 76 and a second position permitting fluid flow from the reservoirs toward the administration set 76, which is substantially identical to that previously described (See FIG. 52). Generally "L"-shaped operating handle 191 includes a groove 191a that closely receives the end portion 188a of operating shaft 188 in the manner shown in FIG. 54. Handle 191 is releasably maintained in its connected position by a handle release member 193 that has locking arms 193a that engage a flat 188b (FIG. 69) formed on the operating handle and the control portion 164 in the manner illustrated in FIGS. 52 and 55.

Figure 57:
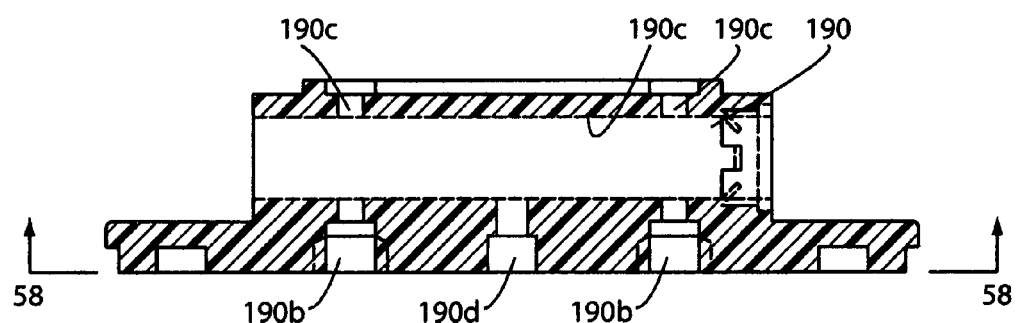
FIG. 57 is a cross-sectional view taken along lines 57-57 of FIG. 56.
Figure 58:
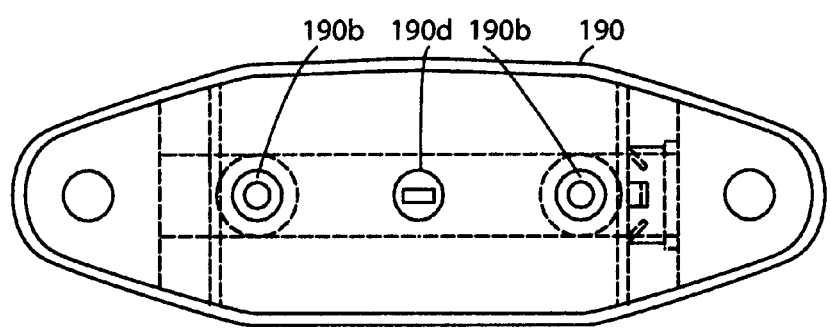
FIG. 58 is a view taken along lines 58-58 of FIG. 57.
Figure 71:
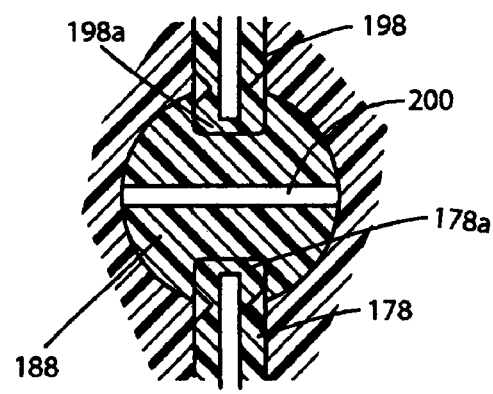
FIG. 71 is an enlarged, cross-sectional view of the operating shaft of the invention as it appears in its first position with the reservoir nipple in the rate control nipple mated with the operating shaft.

Referring to FIGS. 65 through 70, operating shaft 188 can be seen to include a pair of transversely spaced-apart container nipple cavities 194 that are strategically located to receive the upper end portions 178a of container nipples 178 the lower portions of which are received within cavities 190b of reservoir cover 190 (FIG. 57). Operating shaft 188 also includes a pair of transversely spaced-apart rate control nipple cavities 196 that are strategically located to receive the lower end portions 198a of rate control nipples 198 (FIG. 55), the upper portions of which are received within cavities 190c of reservoir cover 190 (FIG. 57). With this construction, as the operating shaft 188 is rotated by the operating handle 191 from it first position shown in FIG. 71 into its second position shown in FIG. 72, end portions 178a of container nipples 178 as well as the end portions 198a of the rate control nipples 198 will be cleanly sheared in the manner depicted in FIG. 72. At the same time, the spaced-apart fluid flow passageways 200 that are formed in operating shaft 188 will move from their first positions (FIG. 71) into their second positions (FIG. 72) thereby opening a fluid flow pathway between reservoirs 175 and the rate control means of the invention via nipples 178 and 198.

Figure 74:
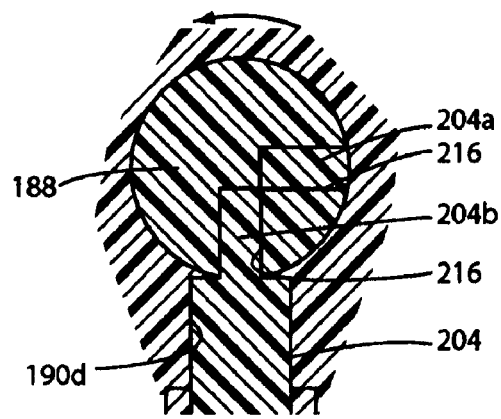
FIG. 74 is a cross-sectional view, similar to FIG. 73, but showing the operating shaft of the invention as it appears rotated into its second position after having sheared the tip of the operating shaft.

As the operating shaft 188 is rotated by the operating handle 191 from it first position into its second position, the tip 204a of a uniquely configured carriage locking shaft 204 will also be cleanly sheared in the manner depicted in FIG. 74. Carriage locking shaft 204, which forms a part of the carriage locking means of the invention, functions to releasably lock carriage 172 in its first position as shown in FIG. 59. As illustrated in FIG. 59, carriage locking shaft 204 extends from operating shaft 188 to carriage 172 and is telescopically movable within a locking shaft tube 208 that extends outwardly from the base 182a of support plate 182. As indicated in FIG. 59, tip 204a passes through a bore 190d formed in reservoir cover 190 and into a cavity 206 formed in the central portion of operating shaft 188 (see also FIGS. 57 and 69), while the opposite end 204b of the locking shaft is in engagement with the locking shaft biasing means of the invention that functions to continuously urge the locking shaft in a direction toward operating shaft 188. The locking shaft biasing means is here provided in the form of a conventional coil spring 210 which also forms a part of the carriage locking means of the invention.

Figure 75:
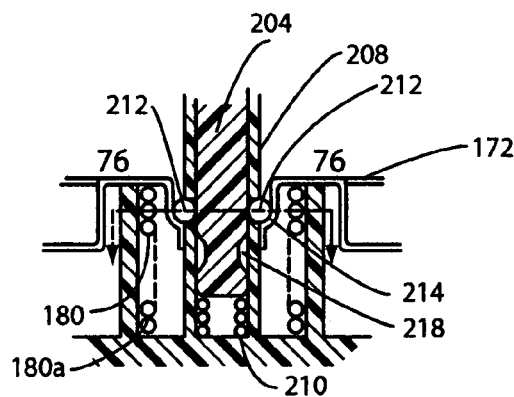
FIG. 75 is a cross-sectional view of the area designated in FIG. 59 as "75".
Figure 77:
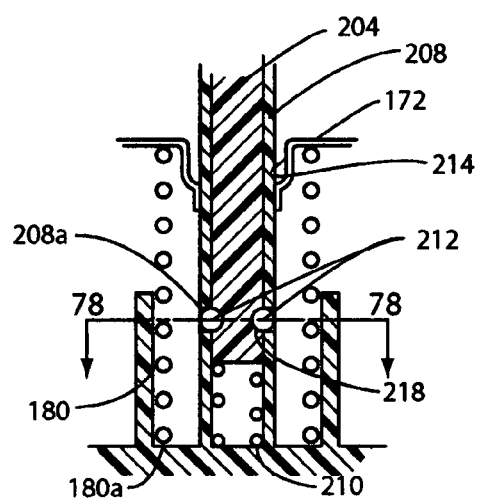
FIG. 77 is a cross-sectional view, similar to FIG. 75, but showing the carriage locking shaft moved into the carriage unlocked position.
Figure 76:
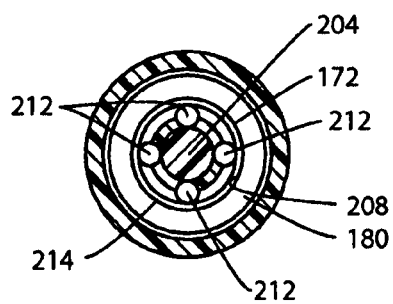
FIG. 76 is a cross-sectional view taken along lines 76-76 of FIG. 75.
Figure 78:
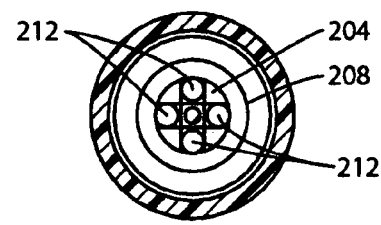
FIG. 78 is a cross-sectional view taken along lines 78-78 of FIG. 77.

As best seen in FIGS. 59 and 75, carriage 172 is locked in its first, or lowered position, by a plurality of carriage locking balls 212 that are initially received within cavities 208a formed in locking shaft tube 208. Carriage locking balls 212 are also received within a centrally located pocket 214 that is formed in carriage 172 (see FIGS. 77, 79, 81 and 82) and circumscribes locking shaft tube 208 in the manner indicated in FIG. 75.

Figure 73:
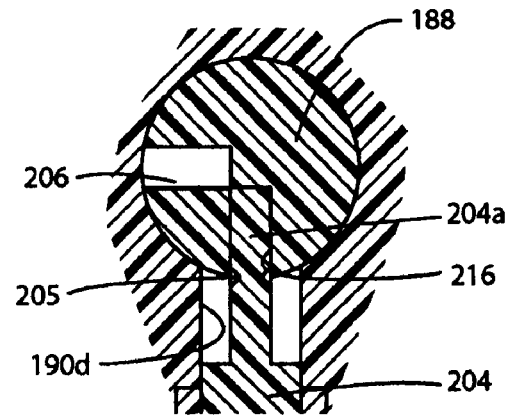
FIG. 73 is an enlarged, cross-sectional view of the operating shaft of the invention as it appears in its first position with the tip of the carriage locking shaft mated with the operating shaft.

When the operating shaft 188 is rotated by the operating handle 191 from its first position into its second position so as to cause the tip 204a of a carriage locking shaft 204 to be cleanly sheared along a score-line 205 (See FIG. 59) in the manner depicted in FIG. 74, coil spring 210 will urge the carriage locking shaft upwardly so that the upper end 204a thereof is received within a cavity 216 that is formed in operating shaft 188 and has been moved into index with the carriage locking shaft (see FIGS. 73 and 74). As the carriage locking shaft moves upwardly in the manner shown in FIG. 77, the carriage locking balls 212 will roll into a groove 218 formed in the carriage locking shaft thereby releasing the carriage and permitting it to move toward its second deployed position due to the urging of the stored energy means, or springs 180.

Upon release of the carriage in the manner described in the preceding paragraph, coil springs 180 will move from their retracted position shown in FIG. 59 to their expanded position shown in FIG. 61, and in so doing will controllably move the carriage from its starting position shown in FIG. 59 to its fully deployed, or extended position shown in FIG. 61.

Figure 83:
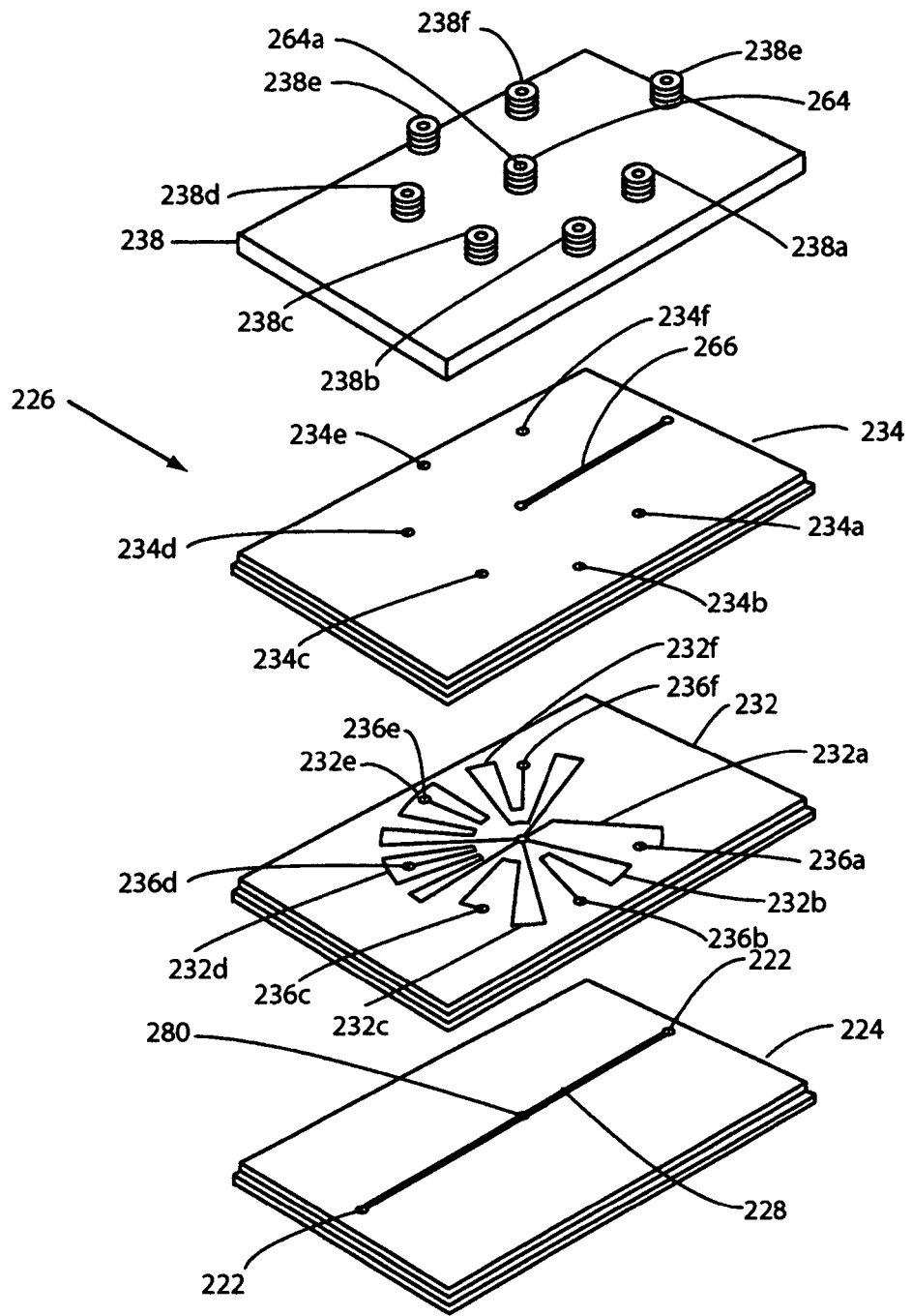
FIG. 83 is a generally perspective, exploded view of the rate control assembly of the apparatus of the invention shown in FIG. 52.
Figure 88:
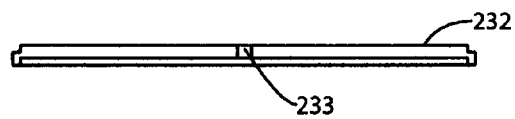
FIG. 88 is a cross-sectional view taken along lines 88-88 of FIG. 87.
Figure 84:
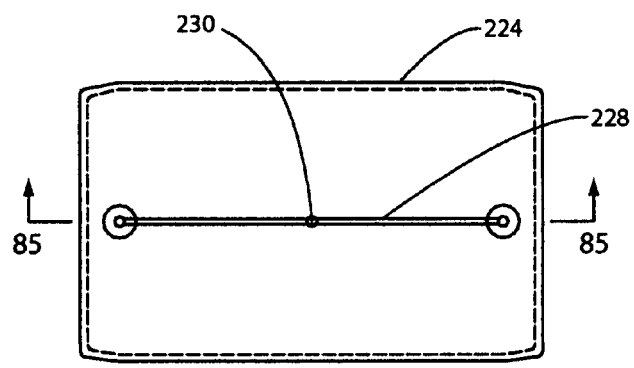
FIG. 84 is a top plan view of the base plate of the rate control assembly shown in FIG. 83.
Figure 86:
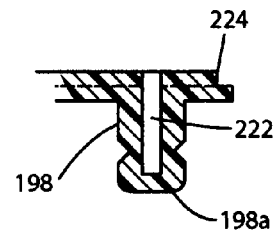
FIG. 86 is a greatly enlarged, cross-sectional view of the area designated in FIG. 85 as "86".
Figure 85:
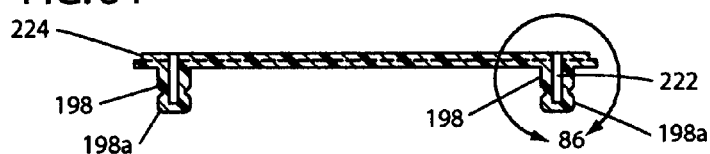
FIG. 85 is a cross-sectional view taken along lines 85-85 of FIG. 84.

As the carriage assembly moves toward its deployed position, the accordion sidewalls 174b of the containers 174 will move into the collapsed configuration shown in FIG. 61 and in so doing will cause the medicinal fluid contained within the containers to be controllably expelled therefrom. The fluid will flow through the central fluid passageways 178p of the container nipples 178, through the spaced-apart fluid flow passageways 200, through the central passageways 198p of the rate control nipples 198 and then into the inlets 222 of the base plate 224 of the rate control assembly 226 (FIGS. 83 and 85). The fluid will then flow through channel 228 and outwardly of outlet 230. From outlet 230 the fluid will flow into the various circuitous fluid channels 232a, 232b, 232c, 232d, 212e and 232f formed in the rate control plate 232 via rate control plate inlet 233 (see FIGS. 83 and 88).

Figure 87:
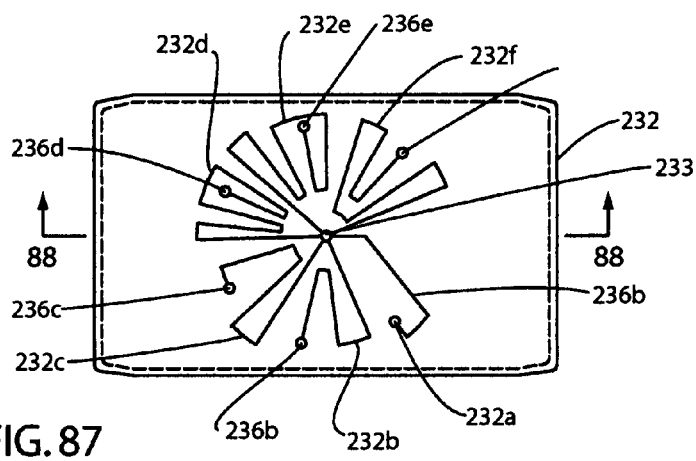
FIG. 87 is a top plan view of the rate control plate of the rate control assembly shown in FIG. 83.
Figure 90:
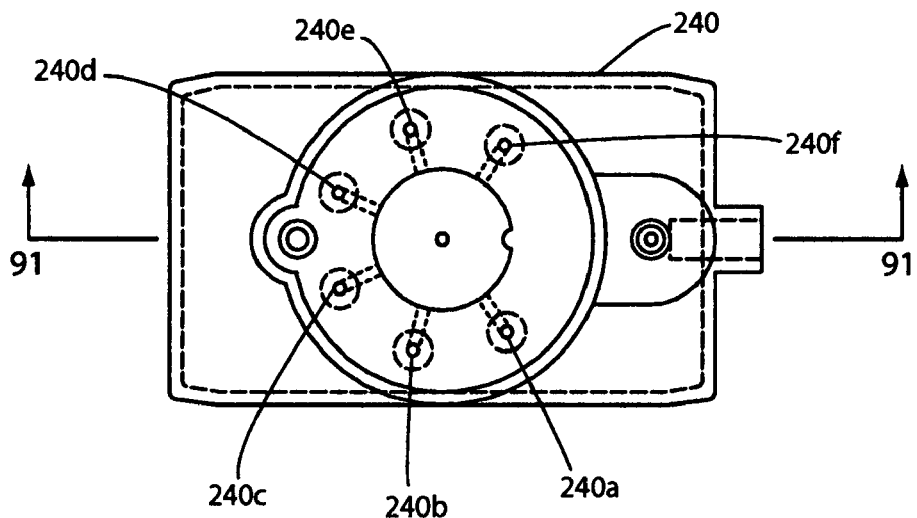
FIG. 90 as a top plan view of the rate control selector housing of the apparatus of the invention shown in FIG. 52.
Figure 91:
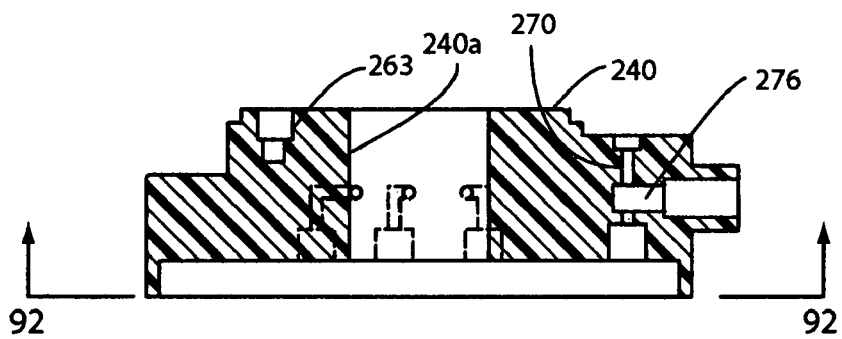
FIG. 91 is a cross-sectional view taken along lines 91-91 of FIG. 90.
Figure 92:
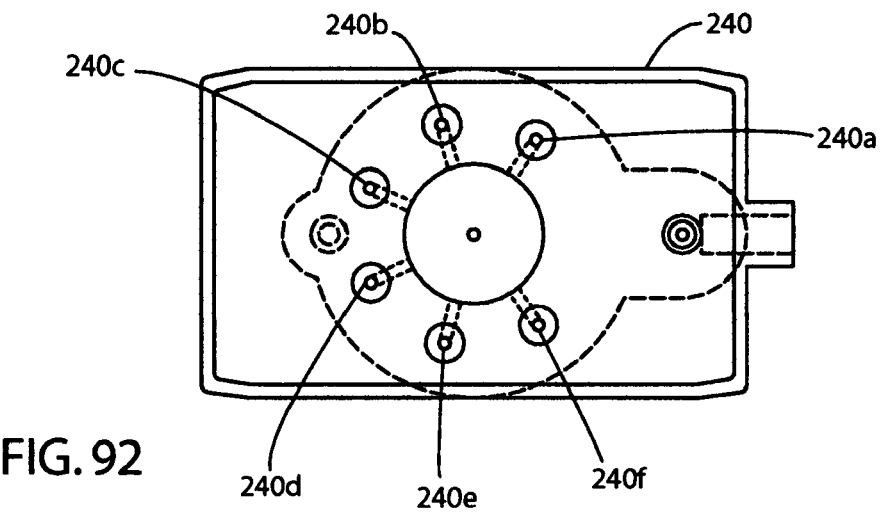
FIG. 92 is a view taken along lines 92-92 of FIG. 91.
Figure 96:
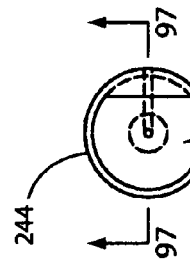
FIG. 96 is a top plan view of the rate control selector member of the apparatus of the invention shown in FIG. 52.
Figure 97:
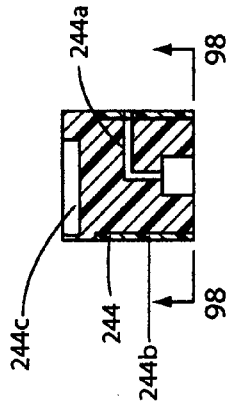
FIG. 97 is a cross-sectional view taken along lines 97-97 of FIG. 96.
Figure 98:
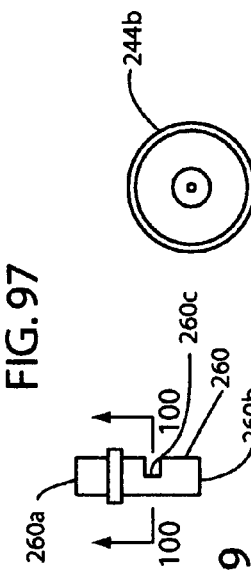
FIG. 98 is a view taken along lines 98-98 of FIG. 97.
Figure 94:
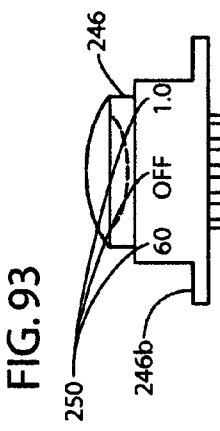
FIG. 94 is a side-elevational view of the rate control knob.
Figure 95:
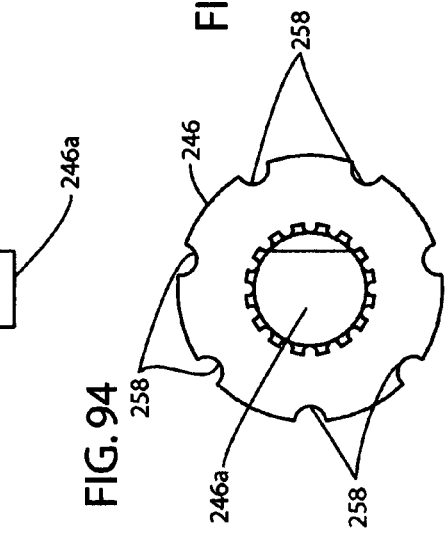
FIG. 95 is a bottom plan view of the rate control knob.

Rate control plate 232, which can be constructed from various plastics, is oriented relative to base plate 224 so that inlet 233 of rate control plate 232 is aligned with the outlet 230 of base plate 224. As each of the channels in the rate control plate fills with the medicinal fluid to be dispensed to the patient, the fluid will flow next into a transfer plate 234 via outlet passageways 236a, 236b, 236c, 236d, 236e and 236f respectively formed in rate control plate (FIG. 87). From the transfer plate 234 the fluid flows into circumferentially spaced-apart outlets of a rate control top plate 238 via circumferentially spaced-apart outlets 234a, 234b, 234c, 234d, 234e and 234f formed in transfer plate 234 (FIG. 83). From the transfer plate the fluid flows into circumferentially spaced-apart outlets 238a, 238b, 238c, 238d, 238e and 238f formed in rate control top plate 238. From outlets 238a, 238b, 238c, 238d, 238e and 238f, the fluid flows into and fills circumferentially spaced-apart, generally "L"-shaped fluid passageways 240a, 240b, 240c, 240d, 240e and 240f formed in a rate control housing 240 that is superimposed over the rate control assembly 226 in the manner shown in FIG. 55. As illustrated in FIGS. 55, 90 and 91, passageways 240a, 240b, 240c, 240d, 240e and 240f are adapted to selectively communicate with a generally "L"-shaped fluid passageway 244a formed in a selector member 244 that is operably associated with a control knob 246 in the manner shown in FIG. 55. Selector member 244, which is provided with an elastomeric coating 244b, is sealably received within a chamber 240g formed in control housing 240 and can be controllably rotated by control knob 246. In this regard, control knob 246 is provided with a shoulder 246a (FIG. 94) that is adapted to engage a mating shoulder 244c formed on Selector member 244 (FIG. 94).

By controllably rotating control knob 246 selector member 244 can be rotated in a manner such that the inlet 244a thereof can be selectively brought into index with one of the fluid passageways 240a, 240b, 240c, 240d, 240e and 240f formed in a rate control housing 240 thereby providing fluid communication with a selected one of the circuitous flow passageways 232a, 232b, 232c, 232d, 232e and 232f formed in the rate control plate 232. Since outlet 244a of the selector member 244 is in fluid communication with the administration set 76 in the manner shown in the drawings, the fluid from the reservoirs 175 can be delivered to the patient at a selected controlled rate of flow.

Figure 89:
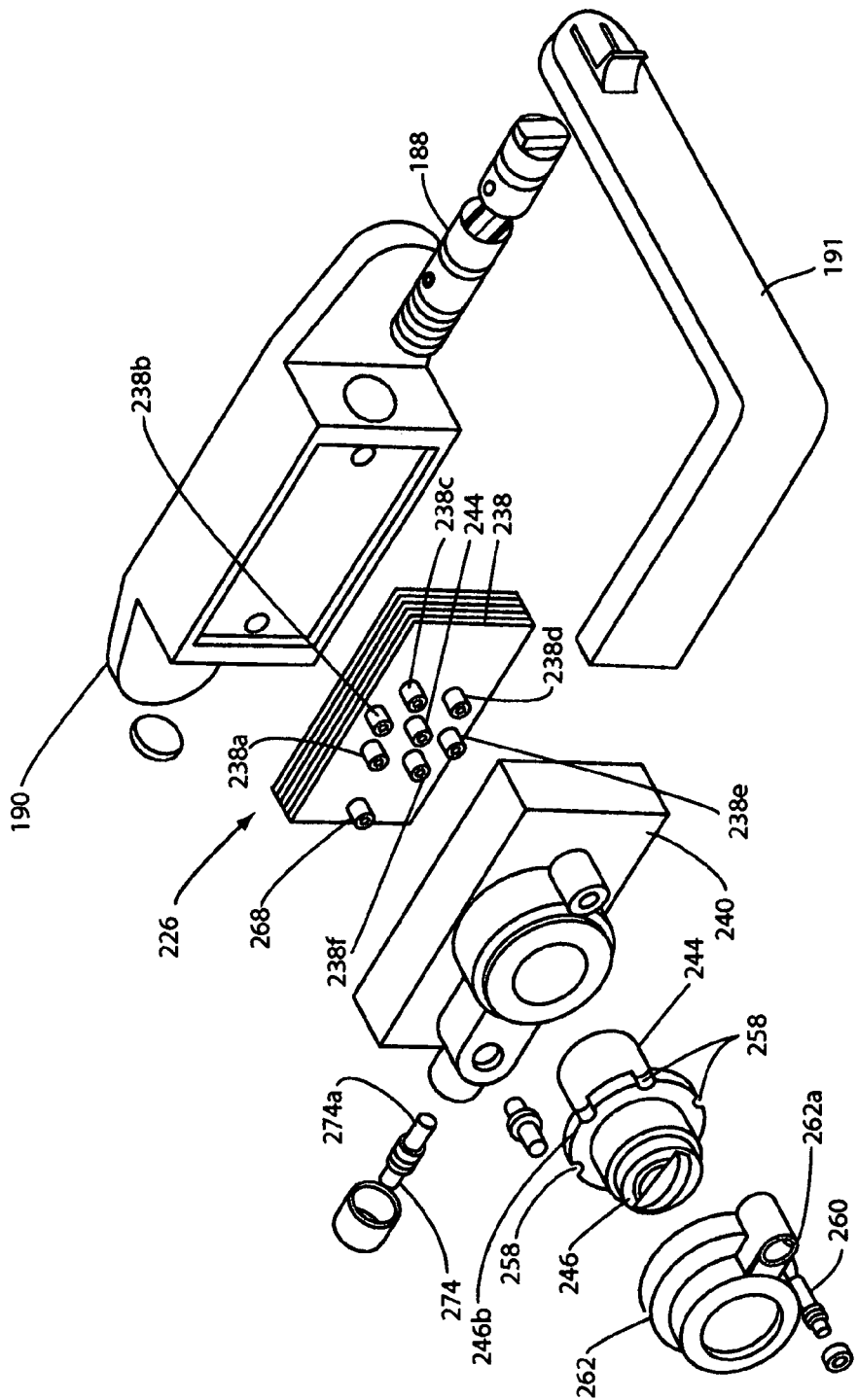
FIG. 89 is a generally perspective, exploded view of the control portion of the apparatus of the invention shown in FIG. 52 that includes the rate control assembly and the operating handle assembly.
Figure 99:
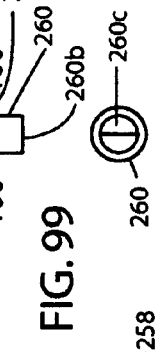
FIG. 99 is a side-elevational view of the indexing shaft of the apparatus of the invention for releasably locking the rate control knob and a selected position.
Figure 100:
FIG. 100 is a cross-sectional view taken along lines 100-100 of FIG. 99.
Figure 93:
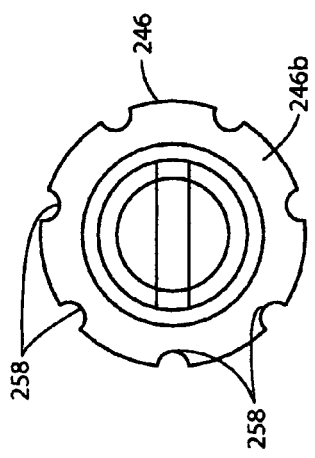
FIG. 93 is a top plan view of the rate control knob of the rate control assembly of the apparatus of the invention shown in FIG. 52.

In operation, after removing a bottom closure cap 247 that has a utility hook 247a (FIG. 53), the apparatus is in the operating configuration shown in FIG. 52. With the fluid reservoirs 175 filled with the medicament to be dispensed to the patient, the dispensing operation can be commenced by rotating the selector knob 246 to the desired flow rate indicated by the indicia 250 imprinted on the body 246c of the selector knob 246, which indicia is viewable through a window 257a formed in a control knob housing 262 that circumscribes the control knob and is supported by rate control housing 240 (see FIG. 55). In this regard, it is to be noted that the rim 246b of the selector knob is provided with a plurality of circumferentially spaced cavities 258 (FIG. 89) that are engagable by an indexing shaft 260 that is carried within a bore 262a formed in control knob housing 262. As best seen in FIGS. 55A and 99, indexing shaft 260, which is biased upwardly be a small coil spring 261, includes a top portion 260a, a bottom portion 260b and is provided with a transverse slot 260c. By exerting a downward pressure on the top surface 260a of the indexing shaft against the urging of spring 261 until the bottom portion of the indexing shaft engages a shoulder 263 formed in the rate control housing, slot 260c can be brought into index with flange portion 246b of the control knob thereby allowing free rotation of the control knob to the desired rate control setting.

With the desired flow rate thusly set, the operating shaft 188 is next rotated through the use of the operating handle 191 from the starting position shown by the solid lines in FIG. 52 to the fully rotated position indicated by the phantom lines in FIG. 52. In this way, communication is opened between the reservoirs 175 and passageways 178a of nipples 178 which, in turn, are in communication with the rate control assembly of the invention via passageway 200 of the operating shaft 188 and passageways 198a of the rate control nipples 198.

After flowing through the various circuitous fluid channels 232a, 232b, 232c, 232d, 232e and 232f formed in the rate control plate 232, the fluid will flow into transfer plate, into the circumferentially spaced-apart outlets 238a, 238b, 238c, 238d, 238e and 238f formed in rate control top plate 238 and into the circumferentially spaced-apart, generally "L"-shaped fluid passageways 240a, 240b, 240c, 240d, 240e and 240f formed in a rate control housing 240. Next, the fluid will flow into the generally "L"-shaped fluid passageway 244a formed in a selector member 244 that is aligned with the selected passageway formed in a rate control housing 240 and then on to the administration set 76 via passageway 264a of the centrally disposed rate control nipple 264 (FIGS. 55 and 83), via fluid passageway 266 formed in transfer plate 234 via transfer nipple 268 and via passageway 270 formed in rate control housing 240. The fluid will then flow onward toward the patient at a precisely controlled rate.

If at any time it is desired to disable the device and render it inert, disable means are provided in the form of a disabling member 274 (FIGS. 55, 89 and 91) that includes a disabling shaft 274a that will block fluid flow through outlet fluid passageway 270 (FIG. 55) when the disabling member is urged inwardly within a cavity 276 formed in the device rate control housing 240 (FIG. 91) causing shaft 274a to intersect and block passageway 270.

Figure 53:
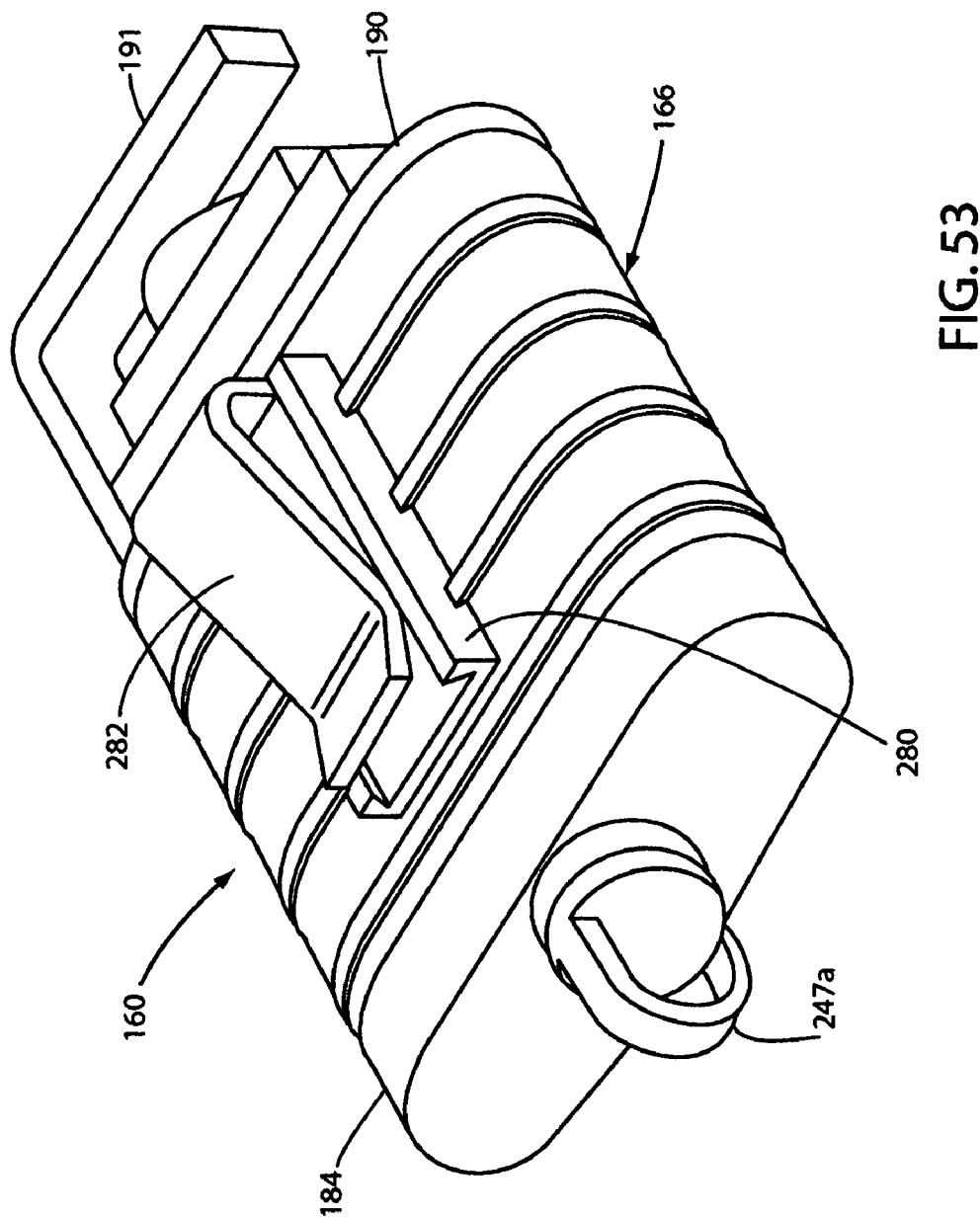
FIG. 53 is a generally perspective, bottom view of the fluid dispensing apparatus shown in FIG. 52.
Figure 56:
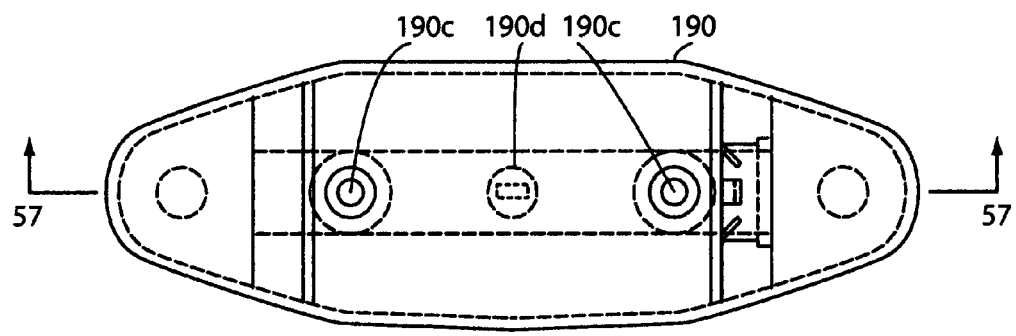
FIG. 56 is a view taken along lines 56-56 of FIG. 55.

As illustrated in FIG. 53, housing 166 is provided with a belt clip receiving member 280 to which a belt clip 282 can be slid ably interconnected. When the belt clip 282 is connected with receiving member 280 the device can be conveniently carried on the user's belt during the medicament dispensing step.

As best seen in FIG. 52, the lower portion 166 of supporting structure 162 also carries consumption determining means for determining the amount of fluid remaining in the reservoirs 175 of the reservoir defining containers 174. This consumption determining means here comprises a consumption gauge 285 that includes a viewing window 285a that enables the user to view the position of the carriage 172 as it travels upwardly due to the urging of springs 180. Indicia 287, which are imprinted on the lower portion 166 of the supporting structure 162 indicate the amount of fluid remaining in the reservoirs of the reservoir defining containers 174 as a function of the position of the carriage 172.

Turning now to FIGS. 101 through 108, still another form of the dispensing apparatus of the present invention for dispensing medicaments to a patient is there shown and generally designated by the numeral 290. This alternate form of the dispensing apparatus is similar in many respects to the previously described embodiments and like numerals are used in FIGS. 101 through 108 to identify like components. The primary difference between this latest form of dispensing apparatus of the invention and that previously described resides in the differently configured fluid reservoir defining containers. More particularly, rather than having bellows-like side walls, the bottle-like collapsible containers 292 of this latest form of the apparatus comprise side walls 292a that telescope in the manner shown in FIGS. 106 and 107 of the drawings.

As in the earlier described embodiments of the invention, the dispensing apparatus here includes a supporting structure 162 which includes an upper control portion 164 and a generally oval-shaped lower portion 166 that is interconnected with the upper portion in the manner best seen in FIG. 103 of the drawings. Disposed within lower portion 166 of the supporting structure is a carriage assembly 170 that is substantially identical in construction and operation to that previously described and functions to support the differently configured reservoir defining assemblies 292 in the manner shown in FIG. 104. Carriage assembly 170 is movable by the stored energy means of the invention, which is also substantially identical in construction and operation to that previously described between a first, lower position shown in FIG. 104 and a second, raised more deployed position wherein the reservoir defining assemblies are moved into the collapsed configuration shown in FIG. 107.

The reservoir defining assemblies 292 each includes a sealed container 294 having a top wall 294a, an telescoping side wall 294b that is connected to top wall 294a and a bottom wall 294c that is connected to telescoping side wall 294b. The sealed containers 294 are preferably formed in accordance with the previously described aseptic blow-fill-seal technique. Each sealed container 294 defines a reservoir 295 that has a combination inlet/outlet 296 (FIG. 106). Combination inlet/outlet 296 is formed by a reservoir nipple 298 having a score-line 299 (See FIG. 108). Reservoir nipple 298 also comprises a part of the reservoir defining assembly 292.

Figure 104:
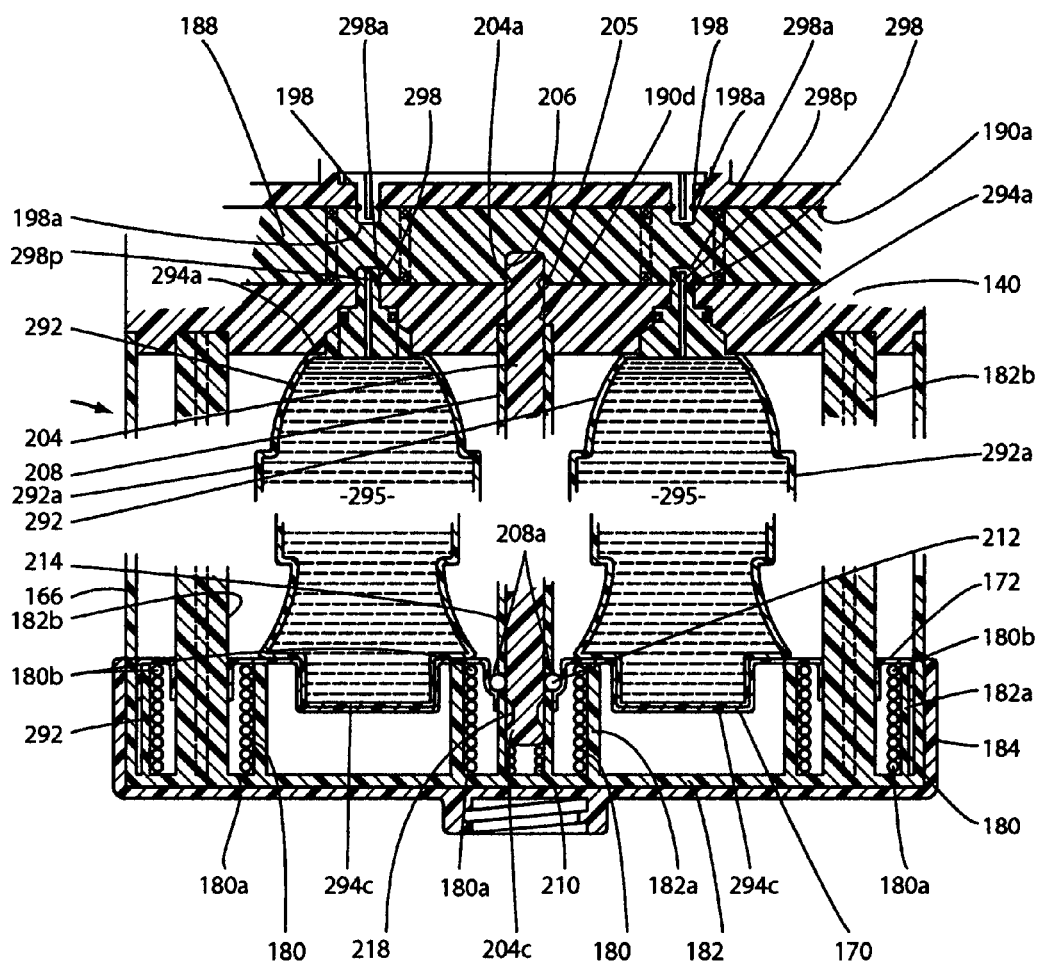
FIG. 104 is a fragmentary, cross-sectional view showing the lower portion of the apparatus.

As in the last described embodiment of the invention, the novel stored energy means, which are operably associated with carriage assembly 170, are provided in the form of three transversely spaced-apart coiled springs 180. As illustrated in FIG. 104, one end 180a of each of the coil springs 180 is disposed in engagement with a generally oval-shaped support plate 182 that is carried by the lower housing 166. Support plate 182 is provided with three transversely spaced-apart, generally cylindrically shaped, cup-like spring receiving portions 182a. The other end 180b of each of the coil springs 180 is disposed in engagement with carriage 172.

As before, support 182 also includes guide means for guiding travel of the carriage assembly between its first locked position shown in FIG. 104 and its second, deployed position. This guide means is substantially identical in construction and operation to that previously described.

When the fluid reservoirs are accessed by the reservoir accessing means of the invention and when the carriage locking means is manipulated in a manner previously described to unlock the carriage, coil springs 180 will move from their retracted position shown in FIG. 104 to their expanded position, and in so doing will controllably move the carriage from its starting position shown in FIG. 104 to its fully deployed, or extended position. Carriage assembly 170 is releasably locked in its first position by a novel locking means, which are also substantially identical in construction and operation for those previously described.

As the carriage assembly moves toward its deployed position, the telescoping sidewalls 292a of the containers 292 will move into the configuration shown in FIG. 107 and in so doing will cause the medicinal fluid contained within the containers to be controllably expelled therefrom.

To further control the flow of medicinal fluid from reservoirs 295 toward the administration set 76 of the invention and then on to the patient, flow control means are provided. As before this novel fluid flow control means, comprises two cooperating components, namely a rate control means for controlling the rate of fluid flow from the collapsible reservoirs to the patient and an operating means for controlling fluid flow between the collapsible reservoirs and the rate control means. Both the rate control means and the operating means of this latest form of the invention are substantially identical in construction and operation to those previously described. The important operating means includes an operating shaft 188 that is controllably rotated by a generally "L"-shaped operating handle 191. As in the earlier described embodiment of the invention, operating shaft 188 rotates within a generally cylindrically shaped chamber 190a formed a reservoir cover member 190 that forms a part of the upper control portion 164 of the supporting structure (FIGS. 55, 56, 57 and 58).

Figure 72:
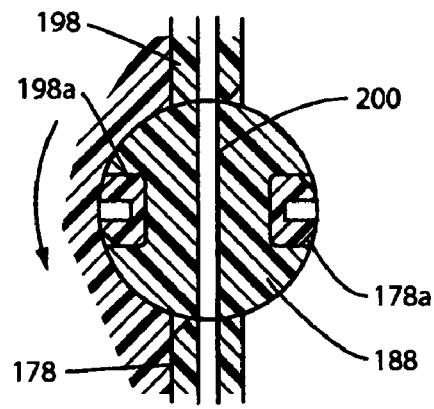
FIG. 72 is a cross-sectional view, similar to FIG. 71, but showing the operating shaft of the invention as it appears rotated into its second position after having sheared the tips of the reservoir nipple and the rate control nipple.
Figure 101:
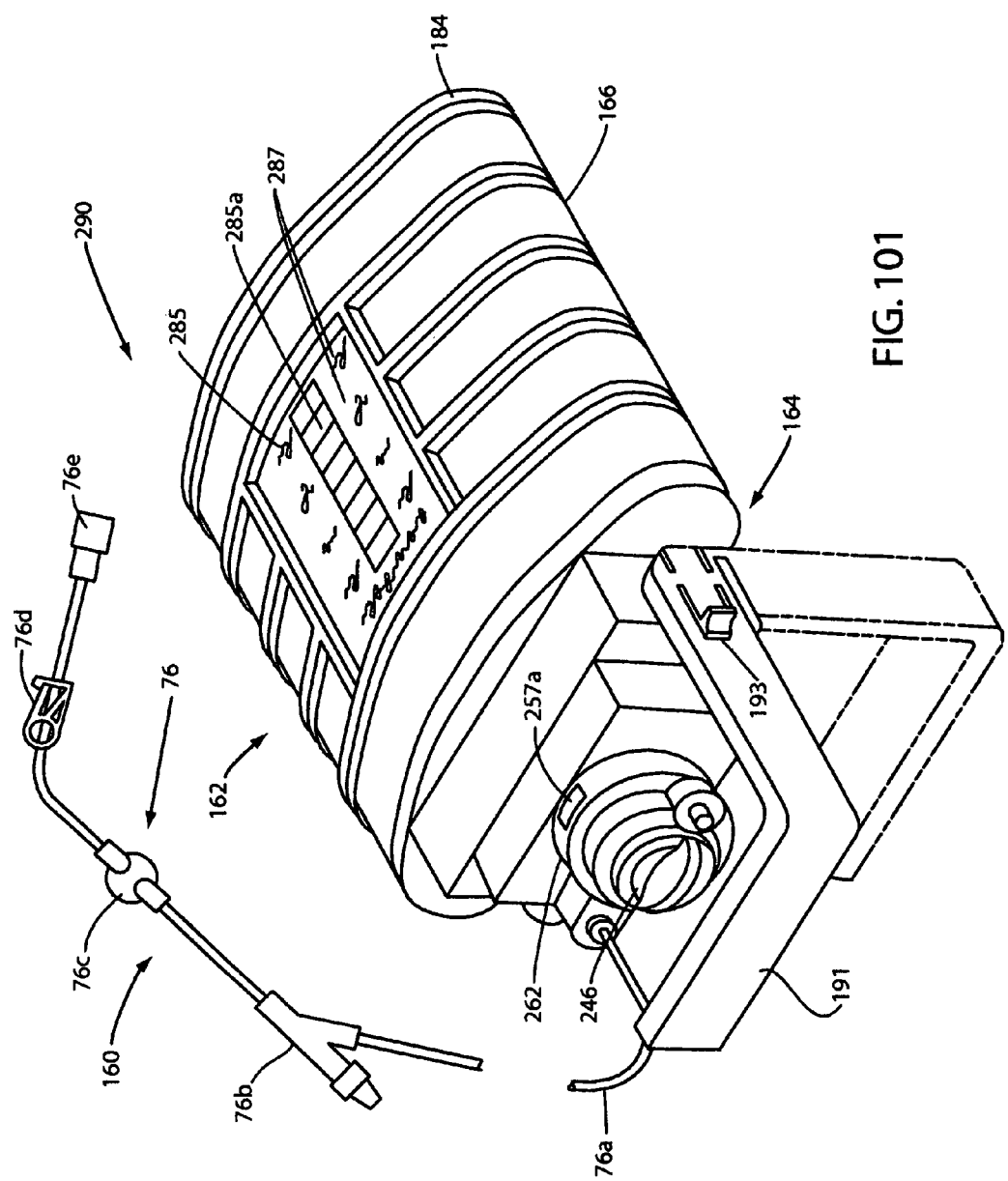
FIG. 101 is a generally perspective, top view of still another version of the fluid dispensing apparatus of the present invention for dispensing medicaments to a patient.

In the operation of the apparatus of this latest form of the invention, as the operating shaft 188 is rotated by the operating handle 191 from it first position into its second position shown in the phantom lines of FIG. 101, end portions 298a of container nipples 298 as well as the end portions 198a of the rate control nipples 198 will be cleanly sheared in the manner depicted in FIG. 72. At the same time, the spaced-apart fluid flow passageways 200 that are formed in operating shaft 188 will move from their first positions (FIG. 71) into their second positions (FIG. 72) thereby opening a fluid flow pathway between reservoirs 295 and the rate control means of the invention via nipples 298 and 198.

As the operating shaft 188 is rotated by the operating handle 191 from it first position into its second position, the tip 204a of a uniquely configured carriage locking shaft 204 will also be cleanly sheared in the manner depicted in FIG. 74. Carriage locking shaft 204, which is also substantially identical in construction and operation to that described in connection with the previously described embodiment, functions to releasably lock carriage assembly 170 in its first position as shown in FIG. 104. As before, and as illustrated in FIG. 107, carriage locking shaft 204 extends from operating shaft 188 to carriage 172 and is telescopically movable within a locking shaft tube 208 that extends outwardly from the base 182a of support plate 182. As indicated in FIG. 103, tip 204a passes through a bore 190d formed in reservoir cover 190 and into a cavity 206 formed in the central portion of operating shaft 188, while the opposite end 204b of the locking shaft is in engagement with the locking shaft biasing means of the invention that functions to continuously urge the locking shaft in a direction toward operating shaft 188. As before, the locking shaft biasing means is here provided in the form of a conventional coil spring 210 which also forms a part of the carriage locking means of the invention.

Carriage 172 is locked in its first, or lowered position, by a plurality of carriage locking balls 212 that are initially received within cavities 208a formed in locking shaft tube 208. Carriage locking balls 212 are also received within a centrally located pocket 214 that is formed in carriage assembly 172 (see FIGS. 79, 81 and 82) and circumscribes locking shaft tube 208 in the manner indicated in FIG. 75. When the operating shaft 188 is rotated by the operating handle 191 from it first position into its second position so as to cause the tip 204a of a carriage locking shaft 204 to be cleanly sheared along a score-line 205 in the manner depicted in FIG. 74, coil spring 210 will urge the carriage locking shaft upwardly so that the upper end 204b thereof is received within a cavity 216 that is formed in operating shaft 188 and has been moved into index with the carriage locking shaft (see FIGS. 73 and 74). As the carriage locking shaft moves upwardly in the manner shown in FIG. 77, the carriage locking balls 212 will roll into a groove 218 formed in the carriage locking shaft thereby releasing the carriage assembly and permitting it to move toward its second deployed position due to the urging of the stored energy means, or springs 180.

Upon release of the carriage assembly in the manner described in the preceding paragraph, coil springs 180 will move from their retracted position shown in FIG. 104 to their expanded position, and in so doing will controllably move the carriage assembly from its starting position shown in FIG. 104 to its fully deployed position.

As the carriage assembly moves toward its deployed position, the telescoping sidewalls 292a of the containers 292 will move into the collapsed configuration shown in FIG. 107 and in so doing will cause the medicinal fluid contained within the containers to be controllably expelled therefrom. The fluid will flow through the central fluid passageways 298p of the container nipples 298, through the spaced-apart fluid flow passageways 200, through the central passageways 198p of the rate control nipples 198 and then into the inlets 222 of the base plate 224 of the rate control assembly 226 (FIG. 85). In the manner previously described, the fluid will then flow through channel 228 and outwardly of outlet 230. From outlet 230 the fluid will flow into the various circuitous fluid channels 232a, 232b, 232c, 232d, 232e and 232f formed in the rate control plate 232 via rate control plate inlet 233 (see FIGS. 83 and 87).

As each of the channels in the rate control plate fills with the medicinal fluid to be dispensed to the patient, the fluid will flow next into a transfer plate 234. From the transfer plate 234 the fluid flows into and fills circumferentially spaced-apart, generally "L"-shaped fluid passageways 240a, 240b, 240c, 240d, 240e and 240f formed in a rate control housing 240 that is superimposed over the rate control assembly 226 in the manner shown in FIG. 55. As illustrated in FIGS. 55, 89, 90 and 97 passageways 240a, 240b, 240c, 240d, 240e and 240f are adapted to selectively communicate with a generally "L"-shaped fluid passageway 244a formed in a selector member 244 that is operably associated with a control knob 246 in the manner shown in FIG. 55. Selector member 244, which is provided with an elastomeric coating 244b, is sealably received within a chamber 240g formed in control housing 240 and, in the manner previously described, can be controllably rotated by control knob 246. Since outlet 244a of the selector member 244 is in fluid communication with the administration set 76 in the manner shown in the drawings, the fluid from the reservoirs 175 can be delivered to the patient at a selected controlled rate of flow in the same manner as described in connection with the previous embodiment of the invention.

As illustrated in FIG. 101, the lower portion 166 of supporting structure 162 of this latest form of the invention also carries consumption determining means for determining the amount of fluid remaining in the reservoir 295 of the reservoir defining containers 292. This consumption determining means, which is substantially identical in construction and operation of that previously described, here comprises a consumption gauge 285 that includes a viewing window 285a that enables the user to view the position of the carriage 172 as it travels upwardly due to the urging of springs 180. Indicia 287, which are imprinted on the lower portion 166 of the supporting structure 162 indicate the amount of fluid remaining in the reservoir defining containers 292 as a function of the position of the carriage 172.

Having now described the invention in detail in accordance with the requirements of the patent statutes, those skilled in this art will have no difficulty in making changes and modifications in the individual parts or their relative assembly in order to meet specific requirements or conditions. Such changes and modifications may be made without departing from the scope and spirit of the invention, as set forth in the following claims.

I claim:

1. A dispensing device for dispensing medicaments to a patient comprising:
   (a) a supporting structure;
   (b) a pair of spaced-apart, pre-filled collapsible containers carried by said supporting structure, each of said containers having a continuous top, bottom and side wall, a shearable nipple connected to and extending from said top wall, said shearable nipple having a severable end portion, said top wall, side wall and bottom wall being formed of a single material, each of said collapsible containers comprising an hermetically sealed reservoir defined by said continuous top, bottom and side walls, said reservoir having an outlet port formed by said shearable nipple and including sealing means for sealing said outlet port;
   (c) stored energy means carried by said supporting structure and operably associated with said collapsible containers for collapsing said collapsible containers to expel fluid therefrom;
   (d) an administration set, including an administration line interconnected with said outlet of said collapsible reservoir; and
   (e) fluid flow control means carried by said supporting structure for controlling fluid flow from said collapsible reservoirs of said collapsible containers toward said administration set, said fluid flow control means comprising operating means for controlling fluid flow from said collapsible container, said operating means comprising an operating shaft rotatably carried by said supporting structure, said operating shaft including a cavity and a spring knife mounted within said cavity for severing said end portion of said shearable nipple.

2. The dispensing device as defined in claim 1 in which said sealing means comprises a pierceable member.

3. The dispensing device as defined in claim 1 in which said sealing means comprises a shearable member.

4. The dispensing device as defined in claim 1 in which said pre-filled collapsible fluid reservoir is aseptically filled and sealed at time of manufacture.

5. The dispensing device as defined in claim 1 in which flow control means comprises rate control means for controlling the rate of fluid flow from said collapsible reservoir toward said administration set.

6. The dispensing device as defined in claim 1 in which said stored energy means comprises a spring operably interconnected with said collapsible containers.

7. The dispensing device as defined in claim 1 further including a carriage for carrying said collapsible containers, said carriage being carried by said supporting structure for movement between a first position and a second position.

8. The dispensing device as defined in claim 1 in which said flow control means comprises rate control means for controlling the rate of fluid flow from said collapsible reservoir toward said administration set and further comprises operating means for controlling fluid flow between said collapsible reservoir and said rate control means.

9. The dispensing device as defined in claim 8 in which said rate control means includes selector means for selecting the rate of fluid flow between said collapsible reservoirs and said administration set.

10. The dispensing device as defined in claim 9 in which said selector means comprises a selector housing carried by said supporting structure and a selector member rotatably carried by said selector housing.

11. A dispensing device for dispensing medicaments to a patient comprising:
  (a) a supporting structure comprising a base assembly and a housing interconnected with said base assembly;
  (b) a carriage assembly interconnected with said supporting structure for movement between a first position and a second position;
  (c) a pair of spaced-apart, unitary pre-filled collapsible containers carried by said carriage assembly, each said container having a top wall and an uninterrupted accordion side wall connected to said top wall and including a reservoir having an outlet port comprising a shearable nipple extending from said top wall, said shearable nipple having a severable end portion;
  (d) a stored energy means operably associated with said carriage assembly for moving said carriage assembly between said first and second positions, said stored energy means comprising a spring;
  (e) an administration set, including an administration line interconnected with said outlet port of said collapsible reservoir; and
  (f) fluid flow control means carried by said base assembly of said supporting structure for controlling fluid flow from said collapsible reservoir toward said administration set, said fluid flow control means comprising rate control means for controlling the rate of fluid flow from said collapsible reservoir and operating means for controlling fluid flow between said collapsible container and said rate control means, said operating means comprising a rotatable operating shaft including a cavity and a cutting member mounted within said cavity for severing said end portion of said shearable nipple.

12. The dispensing device as defined in claim 11, further including locking means carried by said supporting structure for locking said carriage assembly in said first position.

13. The dispensing device as defined in claim 11 in which each said collapsible container comprises an hermetically sealed reservoir.

14. The dispensing device as defined in claim 11 in which said flow control means comprises:
  (a) rate control means carried by said supporting structure for controlling the rate of fluid flow from said collapsible reservoirs toward said administration set; and
  (b) operating means carried by said supporting structure for controlling fluid flow between said collapsible containers and said rate control means.

15. The dispensing device as defined in claim 14 in which said operating means comprises an operating shaft rotatably carried by said base assembly of said supporting structure for movement between a first position blocking fluid flow from said collapsible reservoirs toward said administration set and a second position permitting fluid flow from said collapsible reservoirs toward said administration set.

16. The dispensing device as defined in claim 15 in which each said collapsible container is integrally formed and in which said outlet port of each said reservoir is closed by a frangible member.

17. The dispensing device as defined in claim 16 in which said rate control means includes selector means for selecting the rate of fluid flow between said collapsible reservoirs and said administration set.

18. The dispensing device as defined in claim 17 in which said selector means comprises a selector housing carried by said supporting structure and a selector member rotatably carried by said selector housing.

19. The dispensing device as defined in claim 18 in which said rate control means further includes a rate control plate having a plurality of fluid flow channels interconnected with said outlets of said collapsible reservoirs.

20. A dispensing device for dispensing medicaments to a patient comprising:
  (a) a supporting structure comprising a base assembly and a generally cylindrically shaped outer housing interconnected with said base assembly;
  (b) a carriage assembly interconnected with said supporting structure for movement between a first position and a second position, said carriage assembly comprising a carriage having a carriage base provided with a plurality of transversely spaced-apart openings;
  (c) locking means carried by said supporting structure for locking said carriage assembly in said first position;
  (d) a pair of transversely spaced-apart, aseptically filled collapsible containers carried by said carriage assembly, each said collapsible container being formed by a blow-fill-seal process and each having a continuous wall including a top wall and a collapsible side wall connected to said top wall, said top wall having a severable nipple connected to said top wall;
  (e) a stored energy means operably associated with said carriage assembly for moving said carriage assembly between said first and second positions, said stored energy means comprising a plurality of transversely spaced-apart coil springs, each having a first end in engagement with said supporting structure and a second end in engagement with said carriage;

(f) an administration set, including an administration line interconnected with said outlet port of said collapsible reservoir; and (g) fluid flow control means carried by said base assembly of said supporting structure for controlling fluid flow from said collapsible reservoirs toward said administration set, said flow control means comprising:

(i) rate control means carried by said supporting structure for controlling the rate of fluid flow from said collapsible reservoirs toward said administration set, said rate control means comprising a rate control plate having a plurality of fluid flow channels interconnected with said outlets of said collapsible reservoirs; and (ii) operating means carried by said supporting structure for controlling fluid flow between said collapsible reservoirs and said rate control means, said operating means including a rotatable operating shaft carried by said base assembly, said operating shaft including a cavity and a knife mounted within said cavity for severing said severable nipple.

21. A dispensing device as defined in claim 20 further including guide means connected to said supporting structure for guiding travel of said carriage assembly between said first position and said second position, said guide means comprising a plurality of transversely spaced-apart guide members connected to said base assembly of said supporting structure, said spaced-apart guide members being slidably received within said openings provided in said carriage base.

22. The dispensing device as defined in claim 20 in which said operating shaft is rotatably carried by said base assembly of said supporting structure for movement between a first position blocking fluid flow from said collapsible reservoirs toward said administration set and a second position permitting fluid flow from said collapsible reservoirs toward said administration set.

23. The dispensing device as defined in claim 20 in which each said collapsible container comprises a bellows structure.

24. The dispensing device as defined in claim 20 in which said rate control means further includes selector means for selecting the rate of fluid flow between said collapsible reservoirs and said administration set, said selector means comprising a selector housing carried by said supporting structure and a selector member rotatably carried by said selector housing.

25. The dispensing device as defined in claim 20 in which said locking means comprises:

(a) a locking shaft tube connected to and extending from said supporting structure;

(b) a carriage locking shaft carried by said locking shaft tube for telescopic movement there within between a first position and a second position, said locking shaft having a first end and a second, shearable, end operably associated with said operating shaft;

(c) connector means for releasably connecting said carriage to said locking shaft tube; and (d) locking shaft biasing means carried by said supporting structure for urging said locking shaft to toward said second position.

26. The apparatus as defined in claim 20 in which said carriage includes a locking ball retaining pocket and in which said connector means a plurality of carriage locking balls disposed within said locking ball retaining pocket.

27. The apparatus as defined in claim 20 in which said locking shaft tube includes a plurality of circumferentially spaced cavities and in which said locking balls are received within said circumferentially spaced cavities when said locking shaft is in said first position.

28. The apparatus as defined in claim 27 in which said locking shaft includes a circumferential groove and in which said locking balls are received within said circumferential groove when said locking shaft is in said second position.

\* \* \* \* \*